United States Patent
Ichikawa et al.

(10) Patent No.: US 8,288,077 B2
(45) Date of Patent: Oct. 16, 2012

(54) CHEMICALLY AMPLIFIED RESIST COMPOSITION AND SALT EMPLOYED THEREIN

(75) Inventors: Koji Ichikawa, Toyonaka (JP); Isao Yoshida, Ikeda (JP); Satoshi Yamaguchi, Kawachinagano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 274 days.

(21) Appl. No.: 12/844,557

(22) Filed: Jul. 27, 2010

(65) Prior Publication Data

US 2011/0020749 A1 Jan. 27, 2011

(30) Foreign Application Priority Data

Jul. 27, 2009 (JP) .................. 2009-174792

(51) Int. Cl.
*G03F 7/004* (2006.01)
*C07C 309/00* (2006.01)

(52) U.S. Cl. ............... 430/270.1; 430/910; 430/921; 430/922; 562/41; 562/42; 562/100

(58) Field of Classification Search ............. 430/270.1, 430/910, 921, 922; 562/41, 42, 100
See application file for complete search history.

(56) References Cited

U.S. PATENT DOCUMENTS

| | | | |
|---|---|---|---|
| 6,893,792 B2 | 5/2005 | Miya et al. | |
| 7,301,047 B2 * | 11/2007 | Yoshida et al. | 560/129 |
| 7,304,175 B2 * | 12/2007 | Harada et al. | 560/129 |
| 2003/0194639 A1 | 10/2003 | Miya et al. | |
| 2006/0194982 A1 | 8/2006 | Harada et al. | |
| 2007/0100158 A1 * | 5/2007 | Harada et al. | 560/149 |
| 2008/0076063 A1 | 3/2008 | Yoshida et al. | |
| 2008/0081925 A1 | 4/2008 | Sakamoto et al. | |
| 2008/0193874 A1 * | 8/2008 | Takata et al. | 430/270.1 |

FOREIGN PATENT DOCUMENTS

JP 2004-4561 A 1/2004

\* cited by examiner

*Primary Examiner* — John Chu
(74) *Attorney, Agent, or Firm* — Birch, Stewart, Kolasch & Birch, LLP

(57) ABSTRACT

The object of the present invention is to provide a chemically amplified resist composition excellent in a resolution and a mask error enhancement factor.

By employing the salt represented by the formulae (A1) as an acid generator of a resist composition, the above mentioned object is achieved.

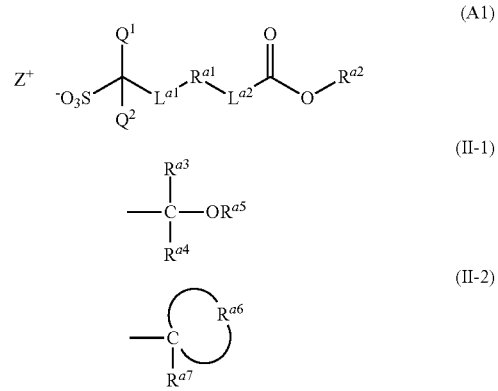

wherein $Z^+$ represents an organic cation, $Q^1$ and $Q^2$ each independently represent a fluorine atom or a perfluoroalkyl group, $R^{a2}$ represents a divalent alicyclic hydrocarbon group pr the like, $R^{a2}$ represents an elimination group represented by the formulae (II-1) or (II-2). In the formulae (II-1) or (II-2), $R^{a3}$ and $R^{a4}$ each independently represent a hydrogen atom or an aliphatic hydrocarbon group, $R^{a5}$ represents an aliphatic hydrocarbon group, $R^{a6}$ represents a divalent aliphatic hydrocarbon group, and $R^{a7}$ represents an aliphatic hydrocarbon group.

9 Claims, No Drawings

CHEMICALLY AMPLIFIED RESIST COMPOSITION AND SALT EMPLOYED THEREIN

FIELD OF THE INVENTION

The present invention relates to a chemically amplified resist composition and a salt employed therein.

BACKGROUND ART

In the field of semiconductors, there is a constant demand for a more sophisticated microfabrication, therefore shortening of the wavelength of light emitted from an exposure light source for photoresists is being proceeded. However, shortening of the wavelength of an emitted light will lead to reduction in exposure intensity. In order to solve this problem, a chemically amplified resist composition that utilizes an acid generator has been developed. High sensitivity can be achieved by the chemically amplified resist composition, since solubilization reactions (in the case of positive resists) and hardening reactions (in the case of negative resists) are accelerated as a result of an acid generated from an acid generator by light irradiation acting as a catalyst. As examples of such acid generators, triphenylsulfonium 1-adamantyl-methoxycarbonyldifluoromethane sulfonate and the like are known (e.g., Example in Japanese Laid-Open Patent Publication No. 2004-4561).

SUMMARY OF THE INVENTION

Accordingly, a high resolution and an improved Mask Error Enhancement Factor are demanded for the chemically amplified resist composition. The present invention focuses on such circumstances, and an object of the present invention is to provide a chemically amplified resist composition excellent in resolution and Mask Error Enhancement Factor.

Through thorough research and study, the inventors of the present invention have found that the above described object could be achieved when a novel salt is used in a resist composition as an acid generator.

The present invention relates to the followings:

[1] A salt represented by the formula (A1):

[Chemical Formula 1]

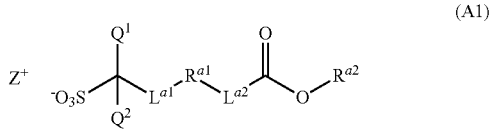

(A1)

wherein $Z^+$ represents an organic cation, $Q^1$ and $Q^2$ each independently represent a fluorine atom or a linear or branched $C_{1-6}$ perfluoroalkyl group, $L^{a1}$ represents —$(CH_2)_{m1}$—, m1 represents an integer ranging from 1 to 6, a methylene group contained in the —$(CH_2)_{m1}$— may be replaced with an oxygen atom (-o-) or a carbonyl group (-co-), at least one hydrogen atom of the —$(CH_2)_{m1}$— may be replaced with a linear or branched $C_{1-4}$ aliphatic hydrocarbon group, $L^{a2}$ represents a single bond, —O—$(CH_2)_{L1}$—, or —CO—O—$(CH_2)_{L1}$—, L1 represents an integer ranging from 1 to 6, a methylene group contained in the —$(CH_2)_{L1}$— group may be replaced with an oxygen atom or a carbonyl group, at least one hydrogen atom of the —$(CH_2)_{L1}$— group may be replaced with a linear or branched $C_{1-4}$ aliphatic hydrocarbon group, $R^{a1}$ represents a $C_{4-36}$ divalent alicyclic hydrocarbon group or a $C_{6-18}$ divalent aromatic hydrocarbon group, and at least one hydrogen atom of the alicyclic hydrocarbon group or the aromatic hydrocarbon group may be replaced with a halogen atom, a linear, branched or cyclic $C_{1-12}$ aliphatic hydrocarbon group, a $C_{7-21}$ aralkyl group, a glycidyloxy group, or a $C_{2-4}$ acyl group, at least one hydrogen atom of the alicyclic hydrocarbon group may be replaced with a $C_{6-20}$ aromatic hydrocarbon group, one or more methylene group contained in the linear, branched or cyclic aliphatic hydrocarbon group, or the aralkyl group may be replaced with an oxygen atom or a carbonyl group, $R^{a2}$ represents an elimination group represented by the formulae (II-1) or (II-2);

[Chemical Formula 2]

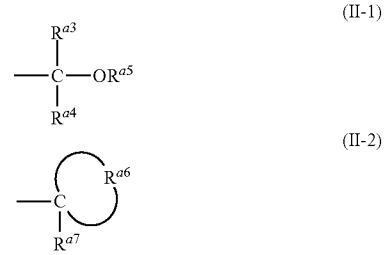

(II-1)

(II-2)

wherein $R^{a3}$ and $R^{a4}$ each independently represent a hydrogen atom or a linear or branched $C_{1-12}$ aliphatic hydrocarbon group, $R^{a5}$ represents a linear, branched or cyclic $C_{1-24}$ aliphatic hydrocarbon group.

In the formula (II-2), $R^{a6}$ represents a $C_{2-24}$ divalent aliphatic hydrocarbon group, and $R^{a7}$ represents a linear or branched $C_{1-12}$ aliphatic hydrocarbon group.

[2] The salt according to [1], wherein $R^{a1}$ is preferably represented by any one of the following formulae (I-1), (I-2), (I-3), or (I-4):

[Chemical Formula 3]

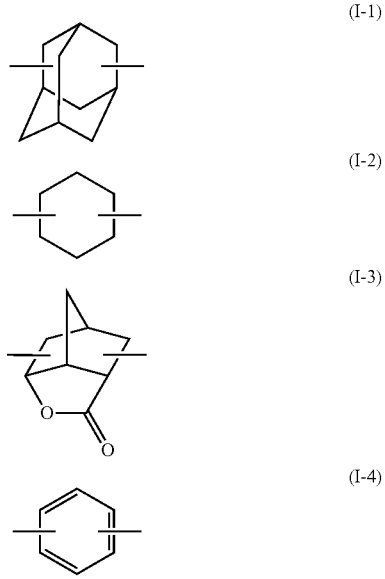

(I-1)

(I-2)

(I-3)

(I-4)

[3] The salt according to [1] or [2], wherein $L^{a1}$ is —CO—O— or —CO—O—$(CH_2)_{k1}$—, and k1 is an integer ranging from 1 to 4.

[4] The salt according to any one of [1] to [3], wherein an anion constituting the salt is represented by any onf formulae (a1-1-1), (a1-1-2), (a1-1-3), (a1-1-4), (a1-1-5), (a1-2-1), (a1-3-1) (a1-4-1), or (a1-5-1);

[Chemical Formula 4]

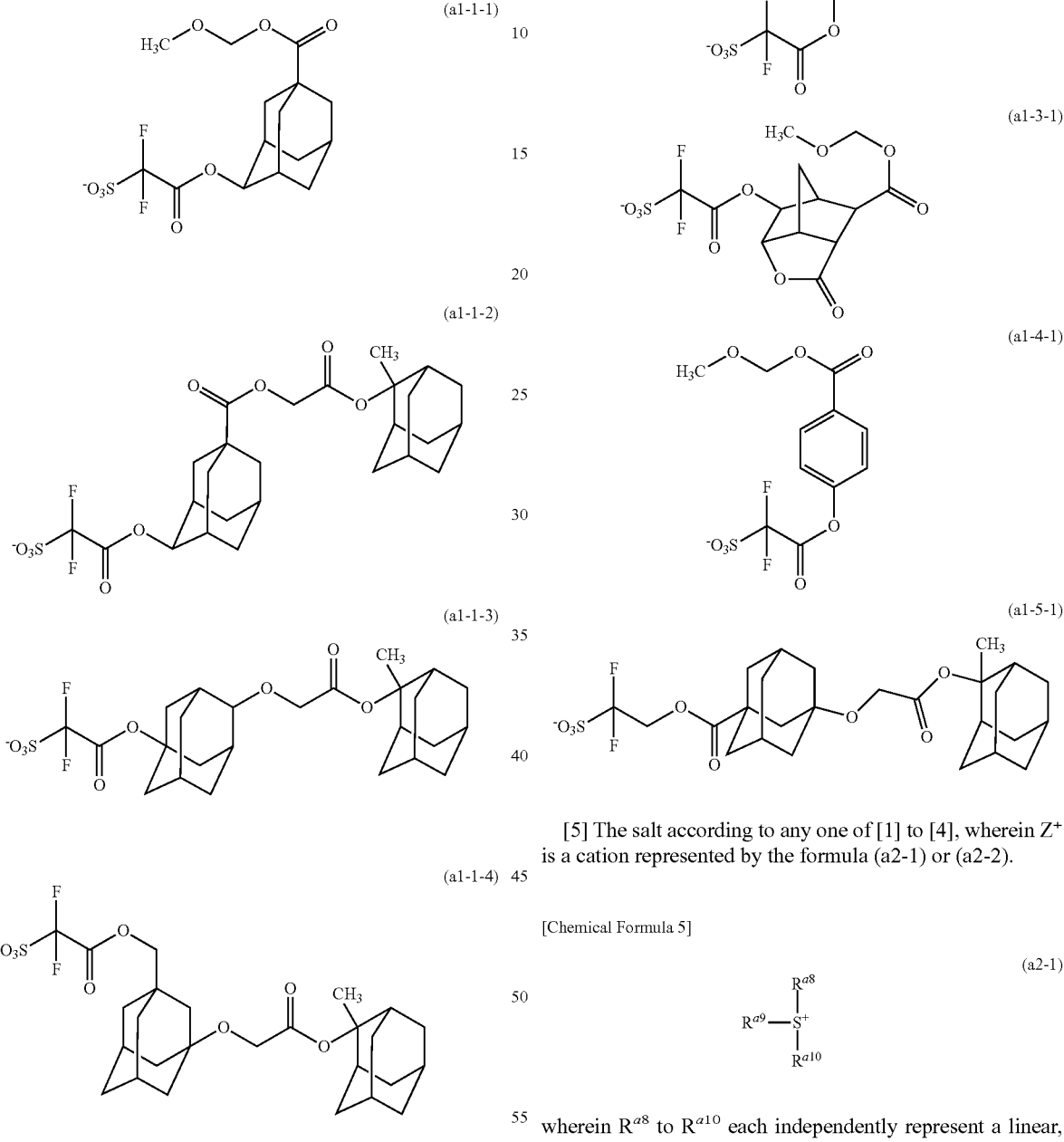

[5] The salt according to any one of [1] to [4], wherein $Z^+$ is a cation represented by the formula (a2-1) or (a2-2).

[Chemical Formula 5]

(a2-1)

wherein $R^{a8}$ to $R^{a10}$ each independently represent a linear, branched or cyclic $C_{1-30}$ aliphatic hydrocarbon group or a $C_{6-18}$ aromatic hydrocarbon group, at least one hydrogen atom of the aliphatic hydrocarbon group or the aromatic hydrocarbon group may be replaced with a halogen atom, a hydroxyl group, a linear or branched $C_{1-12}$ alkoxy group, a glycidyloxy group or a $C_{2-4}$ acyl group, at least one hydrogen atom of the aliphatic hydrocarbon group may be replaced with a $C_{6-18}$ aromatic hydrocarbon group, and the aromatic hydrocarbon group which may constitute any of $R^{a8}$ to $R^{a10}$ may have a linear, branched or cyclic $C_{1-36}$ aliphatic hydrocarbon group as a substituent,

[Chemical Formula 6]

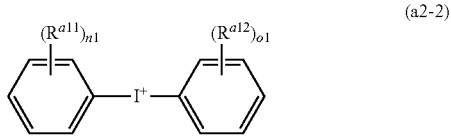

(a2-2)

wherein $R^{a11}$ and $R^{a12}$ each independently represent a hydroxyl group, a linear or branched $C_{1-12}$ aliphatic hydrocarbon group, or a linear or branched $C_{1-12}$ alkoxy group, n1 and o1 each independently represent 0 or 1, when n1 or o1 is 0, it means that corresponding substituent is absent.

[6] The salt according to [5], wherein $Z^+$ is a cation represented by the formula (a2-1-1):

[Chemical Formula 7]

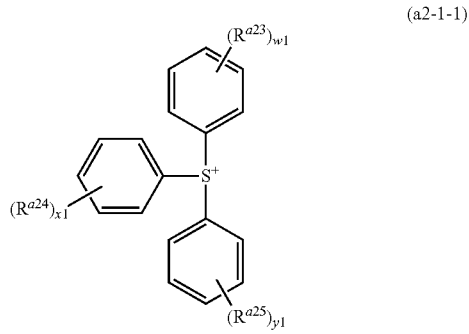

(a2-1-1)

wherein $R^{a23}$ to $R^{a25}$ each independently represent a hydroxyl group, a halogen atom, a linear, branched or cyclic $C_{1-36}$ aliphatic hydrocarbon group, or a linear or branched $C_{1-12}$ alkoxy group, at least one of hydrogen atom of the aliphatic hydrocarbon group may be replaced with a halogen atom, a hydroxyl group, a linear or branched $C_{1-12}$ alkoxy group, a $C_{6-12}$ aromatic hydrocarbon group, a glycidyloxy group or a $C_{2-4}$ acyl group, w1 to y1 each independently represent an integer ranging from 0 to 3, and when any of w1 to y1 represents 0, it means that corresponding $R^{a23}$ to $R^{a25}$ is absent, and when any of w1 to y1 is 2 or more, a plurality of any of $R^{a23}$ to $R^{a25}$ are the same or different from each other.

[7] An acid generator comprising the salt according to any one of [1] to [6].

[8] A resist composition comprising the salt according to any one of [1] to [6] and a resin which becomes soluble in an aqueous alkali solution by the action of an acid. The resist composition of the present invention may further comprise a basic compound.

[9] The resist composition according to [8], further comprising a basic compound.

By employing the salt represented by a formula (A1), a resolution and mask error enhancement factor of a chemically amplified resist composition are further improved comparing to the prior one.

<Salt (A1)>

Hereinafter, a salt of the present invention which is represented by a formula (A1) is explained. In the description of the present invention, the above-described salt represented by the formula (A1) may be simply referred to as "a salt (A1)". A salt, a compound, a monomer and a group represented by another chemical formula may be abbreviated in a similar manner. Further, in the description of the present invention, a chemical formula includes a stereoisomer thereof. As used herein, a "$C_{x-y}$ aliphatic hydrocarbon group" represents an aliphatic hydrocarbon group that has a carbon number of x or more but y or less. However, this carbon number does not include the carbon number of a substituent group (e.g., an aromatic hydrocarbon group or an acyl group) included in the aliphatic hydrocarbon group. A "$C_{x-y}$" in a group other than the aliphatic hydrocarbon group also represents a similar meaning. Furthermore, in the description of the present invention, an "aliphatic hydrocarbon group in which a methylene group is replaced with an oxygen atom or the like" and the like means a "group in which apparently a methylene group of an aliphatic hydrocarbon group is assumed to be substituted with an oxygen atom or the like"; and does not mean a "group obtained, in actuality, by synthesizing an aliphatic hydrocarbon group and then substituting a methylene group with an oxygen atom or the like" and the like. Furthermore, an expression of an "aliphatic hydrocarbon group in which a hydrogen atom is replaced with an alicyclic hydrocarbon group or the like" and the like also has a similar meaning.

A salt (A1) of the present invention has a carboxyl group ($—COOR^{a2}$) which is protected with $R^{a2}$ and the carboxyl group is located at a terminal of a substituent group on an aromatic ring ($R^{a1}$) or a ring of an aliphatic hydrocarbon. This protected carboxyl group releases $R^{a2}$ upon making contact with an acid, and forms a free carboxyl group (—COOH). If such salt (A1) of the present invention is applied to a chemically amplified resist composition as an acid generator, not only the base-solubility of a resin, but also the base-solubility of the acid generator is also enhanced at a light exposed portion of a resist film. Therefore, at the light exposed portion, an increase in the solubility can be observed even at the lower portion of the resist film near the substrate, which results in an enhancement in removability of the resist film during development and an improvement in a shape of a resist pattern, that is, the skirt-like shape is hardly occurred in the resist pattern. As a result, the resolution and Mask Error Enhancement Factor of the resist composition are improved. In the following, formula (A1), which represents the structure of the salt (A1), will be described part by part.

[Chemical Formula 8]

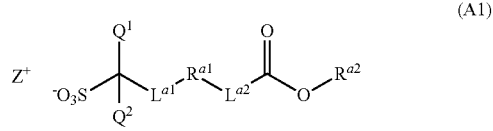

(A1)

In formula (A1), $Q^1$ and $Q^2$ each independently represent a fluorine atom or a $C_{1-6}$ perfluoroalkyl group. Examples of the $C_{1-6}$ perfluoroalkyl group include a perfluoromethyl group, a perfluoroethyl group, a perfluoro-n-propyl group, a perfluoroisopropyl group, a perfluorobutyl group, a perfluoro-sec-butyl group, a perfluoro-tert-butyl group, a perfluoro-n-pentyl group, and a perfluoro-n-hexyl group. Among them, a perfluoromethyl group and a fluorine atom are preferable, and a fluorine atom is more preferable.

In the formula (A1), $L^{a1}$ represents $—(CH_2)_{m1}—$ group, m1 represents an integer ranging from 1 to 6. The methylene chain of $L^{a1}$ may have a linear or branched $C_{1-4}$ aliphatic hydrocarbon group as a side chain. Further, the methylene group contained in $L^{a1}$ may be replaced with an oxygen atom or a carbonyl group. Examples of $L^{a1}$, in which $R^{a1}$ is indicated in order to indicate a bonding direction, include —CO—O—R$^{a1}$ or —CO—O—(CH$_2$)$_{k1}$—R$^{a1}$ (in the formula, k1 represents an integer ranging from 1 to 4, more preferably 1 or 2), and —CO—O—R$^{a1}$ is more preferable.

In the formula (A1), L$^{a2}$ represents, in which R$^{a1}$ is indicated in order to indicate a bonding direction, a single bond, R$^{a1}$—O—(CH$_2$)$_{L1}$— or R$^{a1}$—CO—O—(CH$_2$)$_{L1}$—, L1 represents an integer ranging from 1 to 6. The methylene chain of L$^{a1}$ may have a linear or branched C$_{1-4}$ aliphatic hydrocarbon group as a side chain. Further, the methylene group included in L$^{a1}$ may be replaced with an oxygen atom or a carbonyl group. Preferable L$^{a2}$ is a single bond or R$^{a1}$—O—(CH$_2$)$_{j1}$— (wherein j1 represents 1 or 2), and a single bond is more preferable.

In the formula (A1), R$^{a1}$ is a C$_{4-36}$ divalent alicyclic hydrocarbon group or a C$_{6-18}$ divalent aromatic hydrocarbon group, preferably a C$_{4-36}$ divalent alicyclic hydrocarbon group. The alicyclic hydrocarbon group or the aromatic hydrocarbon group of R$^{a1}$ may have, as a substituent group, a halogen atom, a linear, branched or cyclic C$_{1-12}$ aliphatic hydrocarbon group, a C$_{6-20}$ aromatic hydrocarbon group, a C$_{7-21}$ aralkyl group, a glycidyloxy group, or a C$_{2-4}$ acyl group. Further, a methylene group contained in R$^{a1}$ may be replaced with an oxygen atom or a carbonyl group.

Examples of the halogen atom for the substituent of R$^{a1}$ include a fluorine atom, a chlorine atom, a bromine atom and an iodine atom, a fluorine atom and a chlorine atom are preferable. Examples of the aliphatic hydrocarbon group as a substituent, include a chain aliphatic hydrocarbon group such as a methyl group, an ethyl group, a propyl group, an isopropyl group, a butyl group, a sec-butyl group, a tert-butyl group, a pentyl group, a hexyl group, a heptyl group, a octyl group, a nonyl group, a decyl group, an undecyl group and a dodecyl group; and a cyclic aliphatic hydrocarbon group such as a cyclobutyl group, a cyclopentyl group, a cyclohexyl group, a cycloheptyl group, a cyclooctyl group, a cyclononyl group, and a cyclodecyl group, a norbornyl group, an adamantyl group and an isobornyl group. Examples of the aromatic hydrocarbon group as a substituent include a phenyl group, a biphenylyl group, a naphthyl group. Examples of the aralkyl group as a substituent include a benzyl group, a phenethyl group, a phenylpropyl group, a trityl group, a naphthylmethyl group and a naphthylethyl group. Examples of the acyl group as a substituent include an acetyl group, a propionyl group and a butyryl group. When a plurality of substituents are contained, the plurality of substituents may be the same or different from each other.

The alicyclic hydrocarbon group of R$^{a1}$ may be monocyclic or polycyclic. Examples of the alicyclic hydrocarbon group which is monocyclic include cycloalkanediyl groups (e.g., a cyclopentandiyl group, a cyclohexanediyl group, a cycloheptanediyl group, a cyclooctanediyl group), and cycloalkendiyl groups (e.g., a cyclopentendiyl group, a cyclohexendiyl group, a cycloheptendiyl group, and a cyclooctendiyl group). Examples of the alicyclic hydrocarbon group which is polycyclic include groups obtained by hydrogenating a condensed aromatic hydrocarbon group (e.g., a hydronaphthalenediyl group); and bridged cyclic hydrocarbon groups (e.g., an adamantanediyl group, a norbornanediyl group, a norbornendiyl group). Further, as indicated below, examples of the alicyclic hydrocarbon group of R$^{a1}$ also include groups obtained by condensation of a bridged ring (e.g., a norbornane ring) with a single ring (e.g., a cycloheptane ring or a cyclohexane ring) or a multi-ring (e.g., a decahydronaphthalene ring); and groups obtained by condensation of bridged rings with each other.

[Chemical Formula 9]

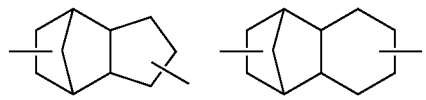

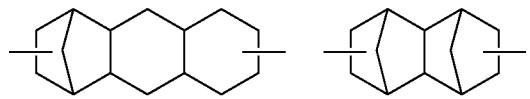

A methylene group included in the alicyclic hydrocarbon group of R$^{a1}$ may be replaced with an oxygen atom or a carbonyl group. The alicyclic hydrocarbon group in which a methylene group is replaced with an oxygen atom (i.e., a group including a cyclic ether) includes an oxolanediyl group (a tetrahydrofuranediyl group), an oxanediyl group (a tetrahydro-2H-pyranediyl group), an oxepanediyl group, and the like. The alicyclic hydrocarbon group in which a methylene group is replaced with a carbonyl group includes a cyclohexanonediyl group, an oxonorbornanediyl group, an oxoadamantanediyl group, and the like. The alicyclic hydrocarbon group in which two adjacent methylene groups are substituted with an oxygen atom or a carbonyl group (i.e., a group including a lactone ring) includes a 2-oxotetrahydrofuranediyl group (a γ-butyrolactonediyl group), a 2-oxotetrahydro-2H-pyranediyl group (a δ-valerolactonediyl group), 2-oxooxepanediyl group (a ε-caprolactonediyl group), and the like. Other alicyclic hydrocarbon groups in which a methylene group is replaced with an oxygen atom or a carbonyl group include the following condensed rings:

[Chemical Formula 10]

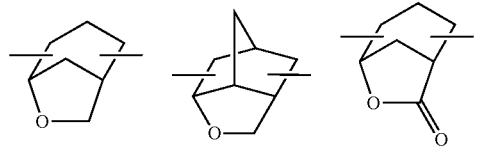

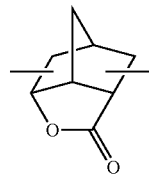

Examples of the aromatic hydrocarbon group of R$^{a1}$ include a phenylene group, a phenanthrenediyl group and an anthracenediyl group.

Among R$^{a1}$ described above, an adamantanediyl group represented by the formula (I-1), a cyclohexanediyl group represented by the formula (I-2), a 5-oxo-4-oxatricyclo[4.2.1.0$^{3,7}$]nonandiyl group represented by the formula (I-3) and a phenylene group represented by the formula (I-4) are preferable, and the adamantanediyl group (I-1) is more preferable.

[Chemical Formula 11]

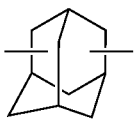
(I-1)

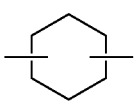
(I-2)

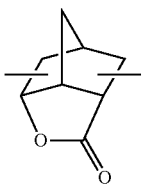
(I-3)

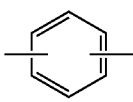
(I-4)

When a position number is given to carbon atoms in such a way that $L^{a1}$ and $L^{a2}$ are numbered in this order, preferable examples of the group (I-1) include an adamantane-1,3-diyl group, an adamantane-1,4-diyl group and adamantane-2,5-diyl group, the adamantane-2,5-diyl group is more preferable. Similarly, when a position number is given to carbon atoms in such a way that $L^{a1}$ and $L^{a2}$ are numbered in this order, a preferable example of the group (I-2) includes a cyclohexane-1,4-diyl group, a preferable example of the group (I-3) includes a 5-oxo-4-oxatricyclo[4.2.1.0$^{3,7}$]nonane-2,9-diyl, a preferable example of the group (I-4) includes a 1,4-phenylene group.

In the formula (A1), $R^{a2}$ is an elimination group represented by the formula (II-1) or (II-2):

[Chemical Formula 12]

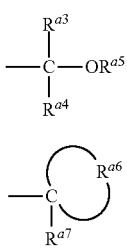

In the formula (II-1), $R^{a3}$ and $R^{a4}$ each independently represent a hydrogen atom or a linear or branched $C_{1-12}$ aliphatic hydrocarbon group. The number of the carbon atom of the aliphatic hydrocarbon group of $R^{a3}$ and $R^{a4}$ is preferably 6 or less, more preferably 4 or less. $R^{a3}$ and $R^{a4}$ each independently is preferably a hydrogen atom or a linear or branched $C_{1-4}$ aliphatic hydrocarbon group (a methyl group, an ethyl group, a propyl group or a butyl group), and more preferably is a hydrogen atom or a methyl group.

In the formula (II-1), $R^{a5}$ represents a linear, branched or cyclic $C_{1-24}$ aliphatic hydrocarbon group. Examples of the aliphatic hydrocarbon group of $R^{a5}$ include the same as those of the substituent described for $R^{a1}$. Preferably, $R^{a5}$ is a linear or branched $C_{1-12}$ aliphatic hydrocarbon group, more preferably is a linear or branched $C_{1-4}$ aliphatic hydrocarbon group (a methyl group, an ethyl group, a propyl group or a butyl group), and further more preferably is a methyl group or a ethyl group.

In the formula (II-2), $R^{a6}$ represents a $C_{2-24}$ divalent aliphatic hydrocarbon group, that is, $R^{a6}$ and the carbon atom bonded by $R^{a6}$ form a cyclic $C_{3-25}$ aliphatic hydrocarbon group. Hereinafter, the cyclic aliphatic hydrocarbon group formed by $R^{a6}$ and the carbon atom bonded by $R^{a6}$ are simply referred to as "a cyclic aliphatic hydrocarbon group of $R^{a6}$".

The cyclic aliphatic hydrocarbon group of $R^{a6}$ may be monocyclic or polycyclic. Examples of the monocyclic hydrocarbon group include cycloalkyl groups (e.g., a cyclopropyl group, a cyclobutyl group, a cyclopentyl group, a cyclohexyl group, a cycloheptyl group and a cyclooctyl group), and cycloalkenyl groups (e.g., a cyclopentenyl group, a cyclohexenyl group, a cycloheptenyl group, and a cyclooctenyl group). Examples of the polycyclic hydrocarbon group include groups obtained by hydrogenating a condensed aromatic hydrocarbon group (e.g., a hydronaphthyl group); and bridged cyclic hydrocarbon groups (e.g., an adamantyl group and a norbornyl group). The bridged cyclic hydrocarbon groups may contains an unsaturated bond in a molecular structure (e.g., a norbornenyl group). Further, as indicated below, examples of the cyclic aliphatic hydrocarbon group also include groups obtained by condensation of a bridged ring (e.g., a norbornane ring) with a single ring (e.g., a cycloheptane ring and a cyclohexane ring) or a multi-ring (e.g., a decahydronaphthalene ring); and groups obtained by condensation of bridged rings with each other:

[Chemical Formula 13]

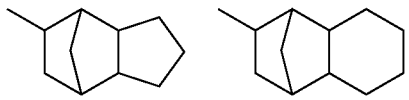

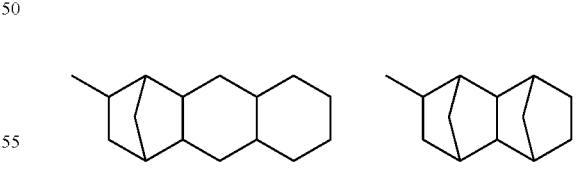

As the alicyclic hydrocarbon group of $R^{a6}$ an adamantyl group and a cyclohexyl group are preferable.

In the formula (II-2), $R^{a7}$ represents a linear or branched $C_{1-12}$ aliphatic hydrocarbon group. The number of the carbon atom of $R^{a7}$ is preferably 6 or less, more preferably 4 or less. Preferred $R^{a7}$ is a linear or branched $C_{1-4}$ aliphatic hydrocarbon group (a methyl group, an ethyl group, a propyl group and a butyl group), and a methyl group or an ethyl group is more preferable.

The salt (A1) of the present invention preferably includes an anion represented by the formulae (a1-1-1), (a1-1-2), (a1-1-3), (a1-1-4), (a1-1-5), (a1-2-1), (a1-3-1), (a1-4-1) or (a1-5-1):

[Chemical Formula 14]

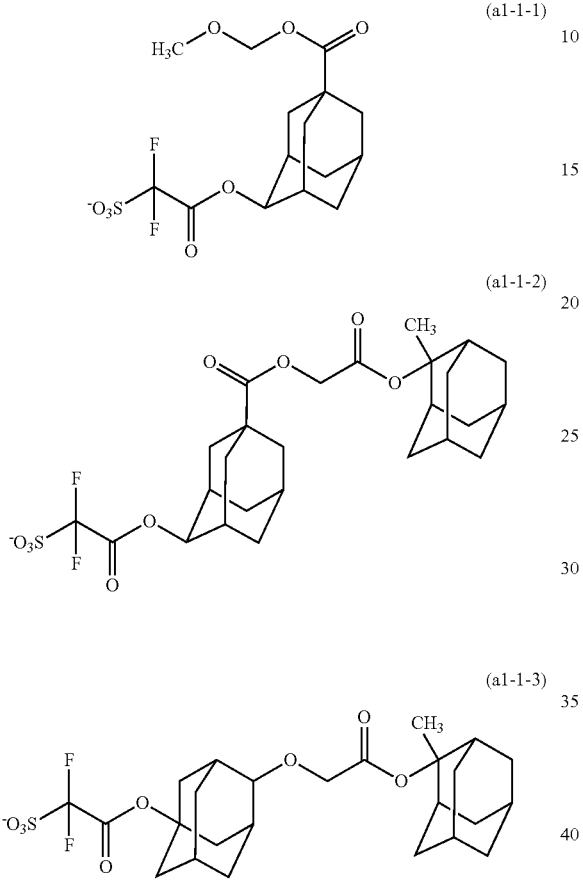

(a1-1-1)
(a1-1-2)
(a1-1-3)
(a1-1-4)
(a1-1-5)

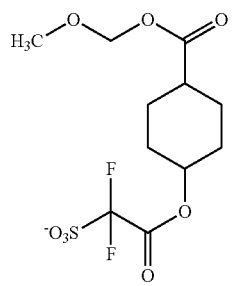

(a1-2-1)

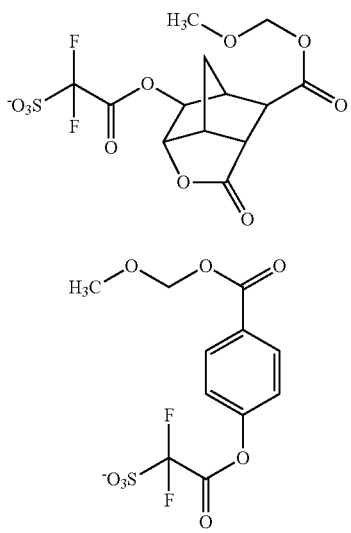

(a1-3-1)

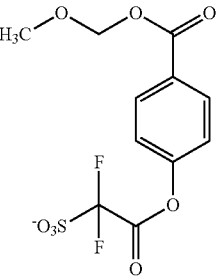

(a1-4-1)

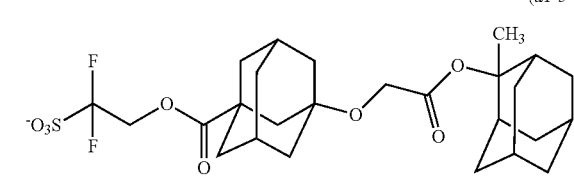

(a1-5-1)

Next, a cation $Z^+$ contained in the salt (A1) will be described. Example of the cation $Z^+$ includes a cation contained in a conventional acid generator such as a sulfonium cation, an iodonium cation, an ammonium cation, a benzothiazolium cation, and a phosphonium cation. Among them, a sulfonium cation and an iodonium cation are preferable, and an arylsulfonium cation is more preferable.

In formula (A1), $Z^+$ is preferably any of cations represented by formulae (a2-1) to (a2-4):

[Chemical Formula 15]

(a2-1)

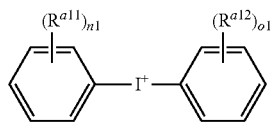

(a2-2)

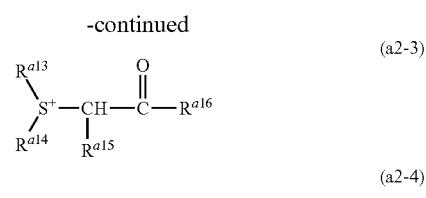

(a2-3)

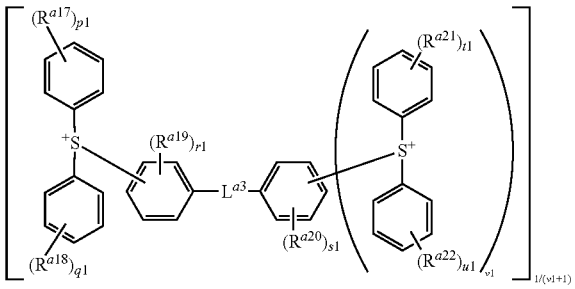

(a2-4)

In formula (a2-1), $R^{a8}$ to $R^{a10}$ each independently represent a linear, branched or cyclic $C_{1-30}$ aliphatic hydrocarbon group, or a $C_{6-20}$ aromatic hydrocarbon group. At least one hydrogen atom of the aliphatic hydrocarbon group or the aromatic hydrocarbon group may be replaced with a halogen atom, a hydroxyl group, a linear or branched $C_{1-12}$ alkoxy group, a glycidyloxy group or a $C_{2-4}$ acyl group. Further, at least one hydrogen atom of the aliphatic hydrocarbon group may be replaced with a $C_{6-18}$ aromatic hydrocarbon group, and the aromatic hydrocarbon group may have a linear, branched or cyclic $C_{1-36}$ aliphatic hydrocarbon group as a substituent. Specific examples of the aliphatic hydrocarbon group, the aromatic hydrocarbon group, the alkoxy group and the acyl group contained in the cation $Z^+$ include the same as described above.

In formula (a2-2), $R^{a11}$ and $R^{a12}$ each independently represent a hydroxyl group, a linear or branched $C_{1-12}$ aliphatic hydrocarbon group (preferably a $C_{1-12}$ alkyl group, more preferably a $C_{1-6}$ alkyl group) or a linear or branched $C_{1-12}$ alkoxy group (preferably a $C_{1-6}$ alkoxy group, more preferably a methoxy group or an ethoxy group). "n1" and "o1" each independently represent 0 or 1. When n1 is 0, it means that $R^{a11}$ is absent. When o1 is 0, it means that $R^{a12}$ is absent.

In formula (a2-3), $R^{a13}$ and $R^{a14}$ each independently represent a linear or branched $C_{1-12}$ aliphatic hydrocarbon group (preferably a $C_{1-12}$ alkyl group, more preferably a $C_{1-6}$ alkyl group), or a cyclic $C_{3-12}$ aliphatic hydrocarbon group (preferably a $C_{3-12}$ cycloalkyl group, more preferably a $C_{3-6}$ cycloalkyl group, even more preferably a cycloheptyl group or a cyclohexyl group). $R^{a15}$ represents a hydrogen atom, a linear or branched $C_{1-12}$ aliphatic hydrocarbon group, and preferably is a hydrogen atom. $R^{a16}$ represents a linear or branched $C_{1-12}$ aliphatic hydrocarbon group (preferably a $C_{1-12}$ alkyl group, and more preferably a $C_{1-6}$ alkyl group), a cyclic $C_{3-12}$ aliphatic hydrocarbon group (preferably a $C_{3-12}$ cycloalkyl group, and more preferably a $C_{3-6}$ cycloalkyl group), or a $C_{6-20}$ aromatic hydrocarbon group (preferably a phenyl group or a naphthyl group). The aromatic hydrocarbon group of $R^{a16}$ may have a substituent such as a linear or branched $C_{1-12}$ aliphatic hydrocarbon group, a hydroxyl group, and a linear or branched $C_{1-12}$ alkoxy group, or the like.

In the formula (a2-3), $R^{a13}$ and $R^{a14}$ may be bonded to each other and $R^{a15}$ and $R^{a16}$ may be bonded to each other such that three- to twelve-membered rings (preferably, three- to six-membered rings) are formed, and a methylene group in any of the rings may be replaced with an oxygen atom (—O—), a sulfur atom (—S—), or a carbonyl group (—CO—). Examples of the ring formed by $R^{a13}$ and $R^{a14}$ include a thiolane-1-ium ring (a tetrahydrothiophenium ring), a thian-1-ium ring, and a 1,4-oxathian-4-ium ring. Examples of the ring formed by $R^{a15}$ and $R^{a16}$ include an oxocycloheptane ring, an oxocyclohexane ring, an oxonorbornane ring, and an oxoadamantane ring.

In the formula (a2-4), $R^{a17}$ to $R^{a22}$ each independently represent a hydroxyl group, a linear or branched $C_{1-12}$ aliphatic hydrocarbon group (preferably a $C_{1-12}$ alkyl group, more preferably a $C_{1-6}$ alkyl group, further more preferably a methyl group, an ethyl group or tert-butyl group), or a linear or branched $C_{1-12}$ alkoxy group (preferably a $C_{1-6}$ alkoxy group, more preferably a methoxy group or an ethoxy group). $L^{a3}$ represents a sulfur atom or an oxygen atom. "p1" to "u1" each independently represent an integer ranging from 0 to 2, and v1 represents 0 or 1. When any of p1 to v1 are 0, it means that the corresponding substituents are absent. When any of p1 to v1 are 2, a plurality of $R^{a17}$ to $R^{a22}$, respectively, may be the same or different from each other.

Among the cations (a2-1) to (a2-4), the cation (a2-1) is preferable, and a cation represented by the following formula (a2-1-1) is more preferable.

[Chemical Formula 16]

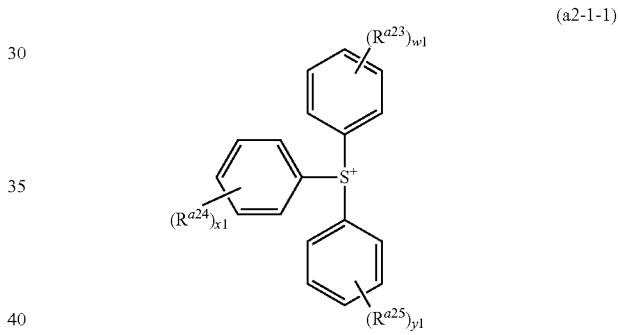

(a2-1-1)

In formula (a2-1-1), $R^{a23}$ to $R^{a25}$ each independently represent a hydroxyl group, a halogen atom (preferably a fluorine atom), a linear, branched or cyclic $C_{1-36}$ aliphatic hydrocarbon group (preferably a linear or branched $C_{1-12}$ aliphatic hydrocarbon group, and more preferably a methyl group, an ethyl group, a propyl group (especially isopropyl group), a butyl group (especially tert-butyl group), a pentyl group, a hexyl group, a heptyl group, or an octyl group), or a linear or branched $C_{1-12}$ alkoxy group (preferably a $C_{1-6}$ alkoxy group). The aliphatic hydrocarbon group of $R^{a23}$ to $R^{a25}$ may have a halogen atom, a hydroxyl group, a linear or branched $C_{1-12}$ alkoxy group, a $C_{1-12}$ aromatic group, a glycidyloxy group or a $C_{2-4}$ acyl group as a substituent group. "w1", "x1" and "y1" each independently represent an integer ranging from 0 to 3 (preferably 0 or 1). When w1 is 0, it means that $R^{a23}$ is absent, when x1 represents 0, it means that $R^{a24}$ is absent, and when y1 represents 0, it means that $R^{a25}$ is absent. When any of w1 to y1 is 2 or more, a plurality of $R^{a23}$ to $R^{a25}$, respectively, may be the same or different from each other. Among the cation (a2-1-1), triphenylsulfonium cation, tris(p-tolyl)sulfonium cation, and 4-tert-butylphenyldiphenylsulfonium cation are preferable.

Next, specific examples of the cation contained in the salt (A1) will be described. Firstly, specific examples of the cation (a2-1-1) are as follows:

[Chemical Formula 17]
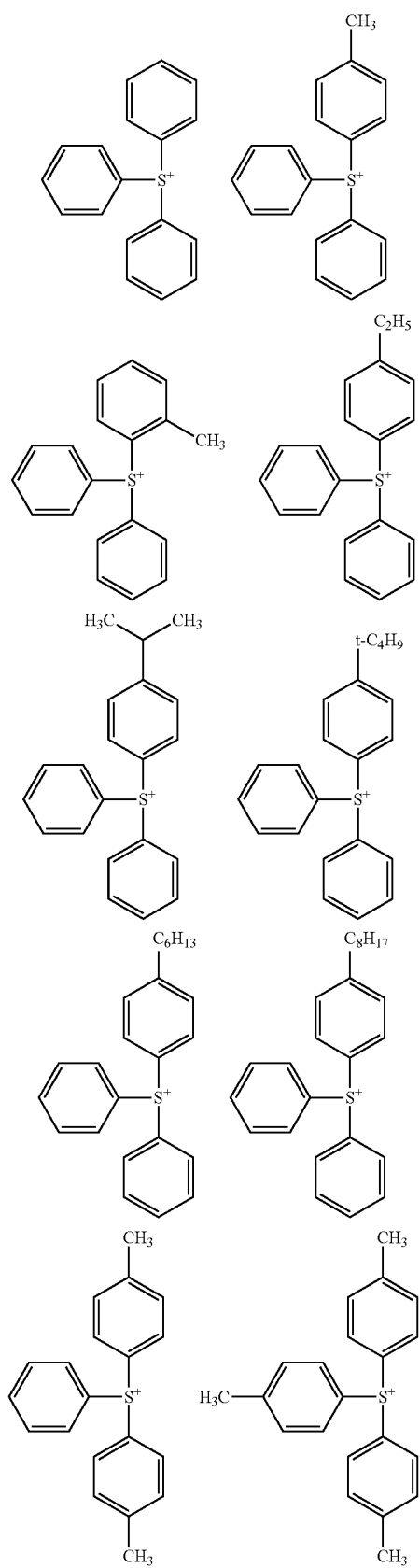
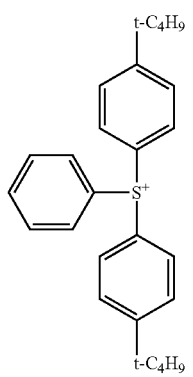
[Chemical Formula 18]
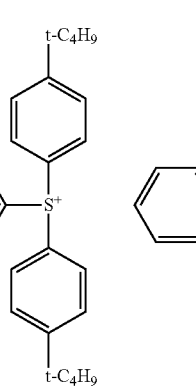
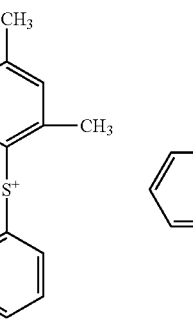
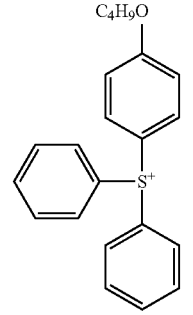

-continued
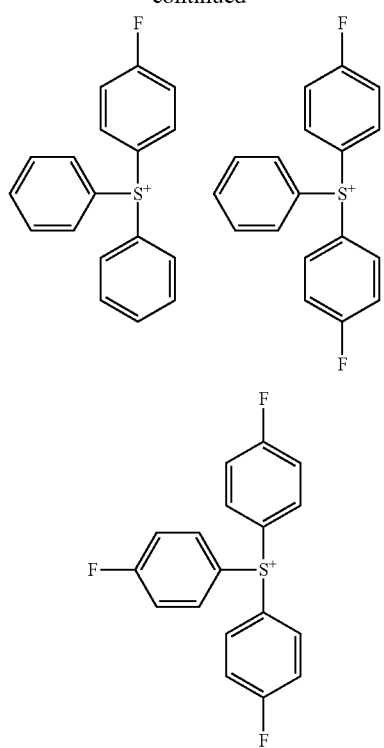
Specific examples of the cation (a2-2) are as follows:
[Chemical Formula 19]
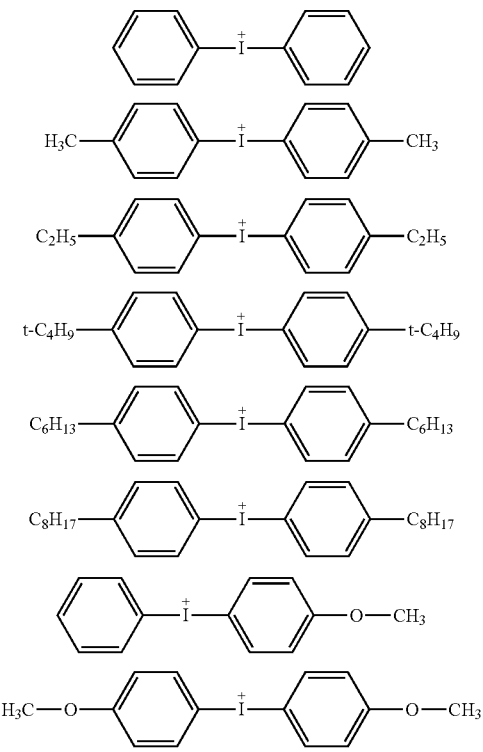
Specific examples of the cation (a2-3) are as follows:
[Chemical Formula 20]
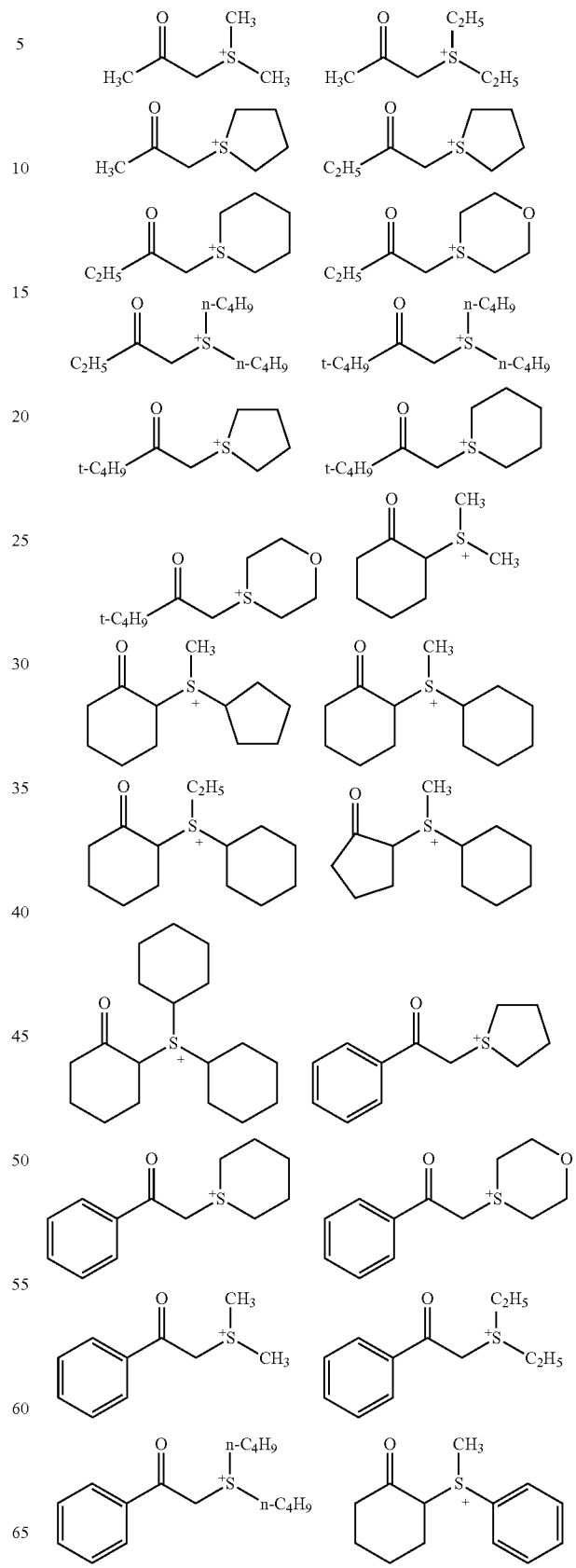

[Chemical Formula 21]
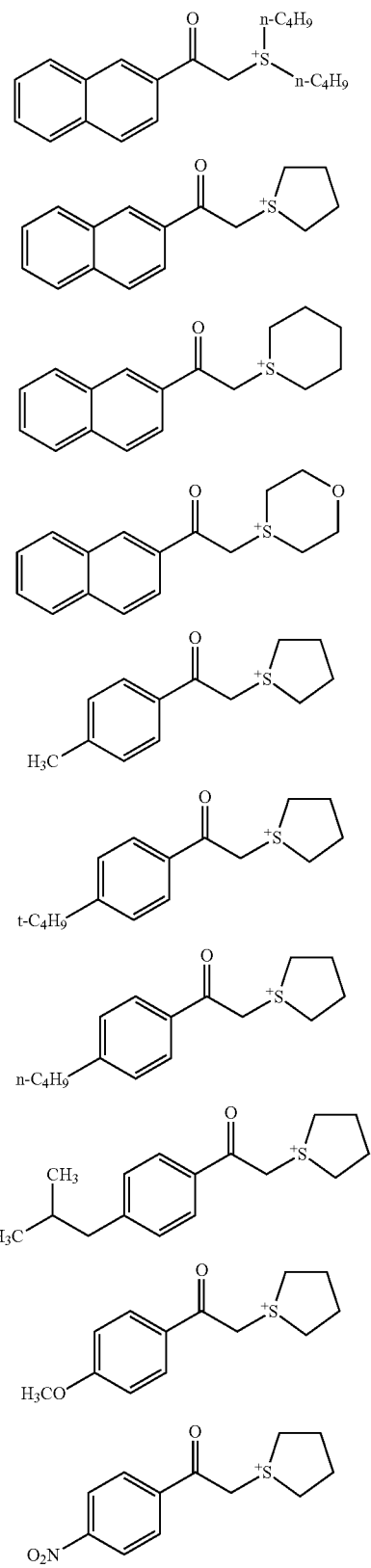
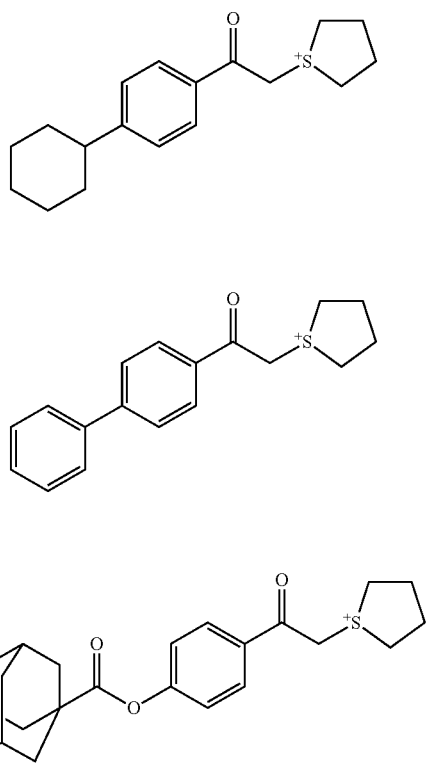
Specific examples of the cation (a2-4) are as follows:
[Chemical Formula 22]
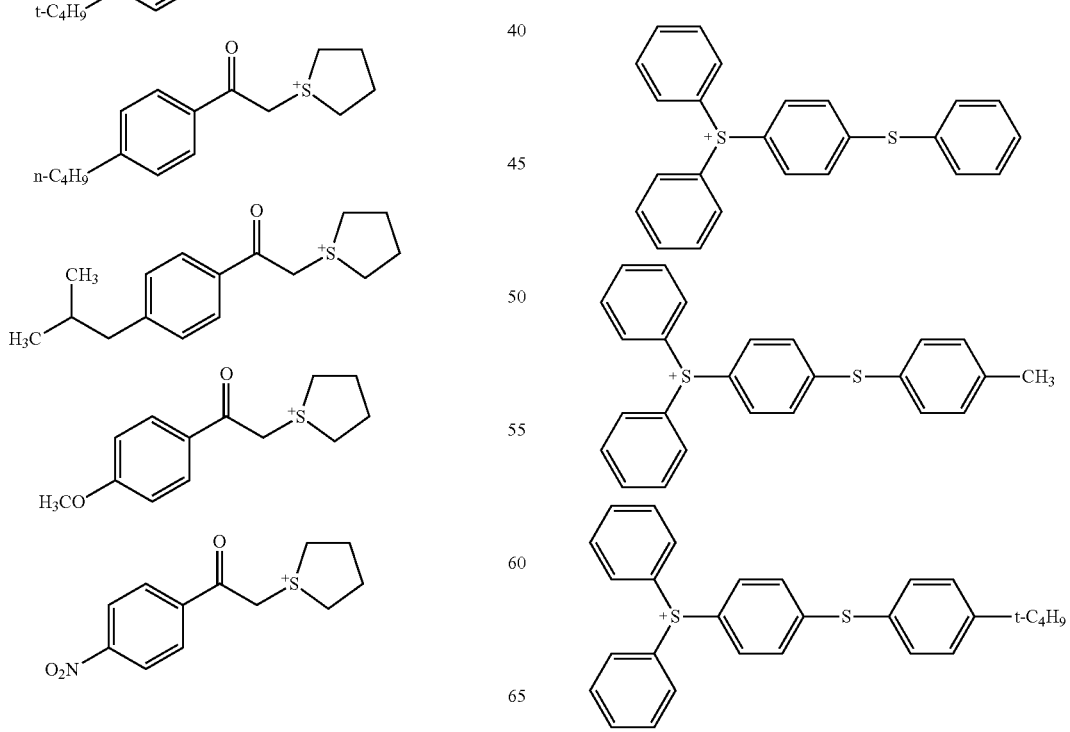

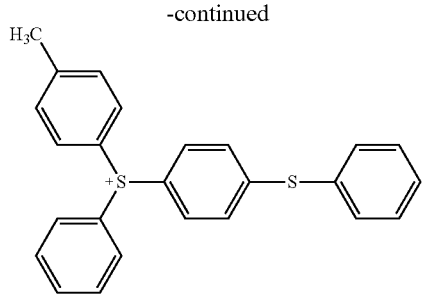
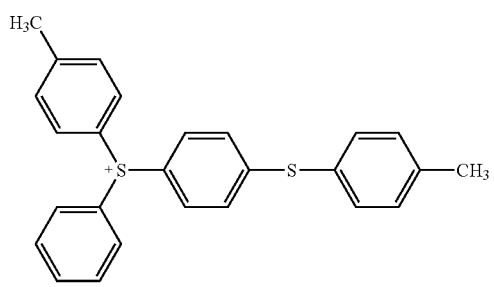
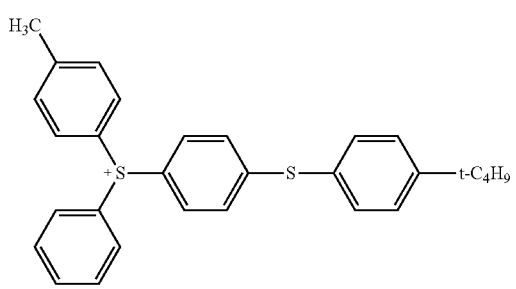
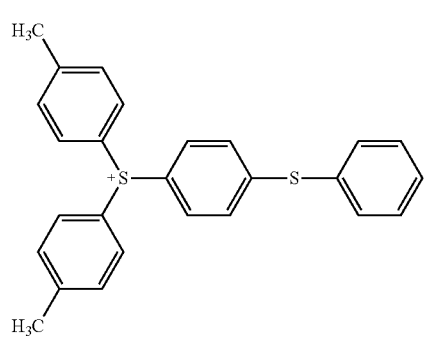
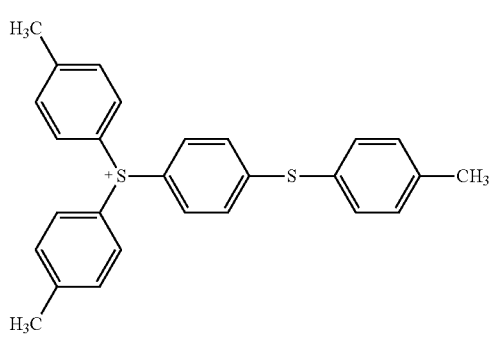
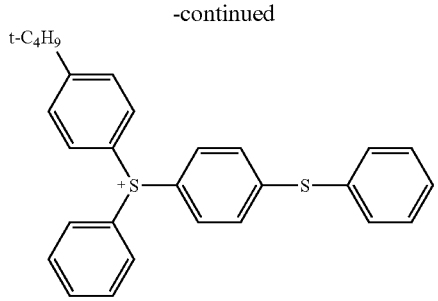
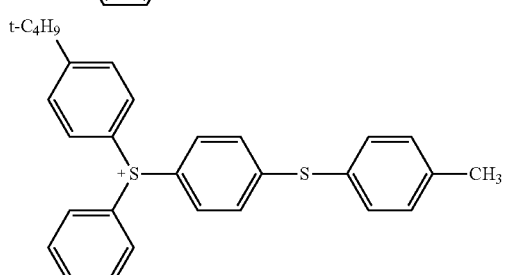
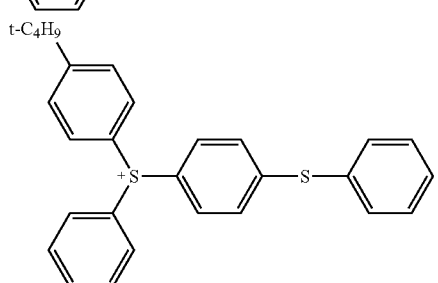
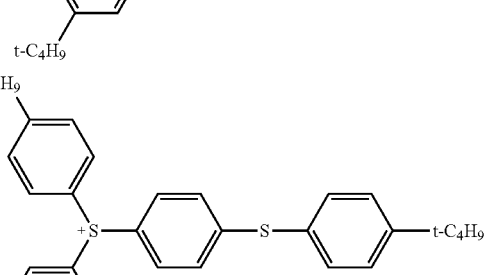
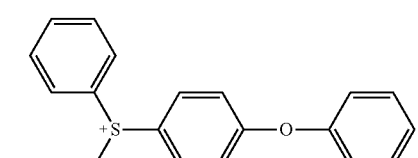
[Chemical Formula 23]
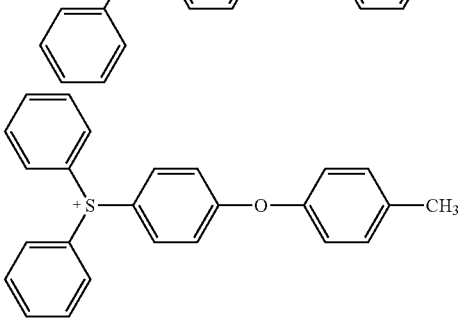

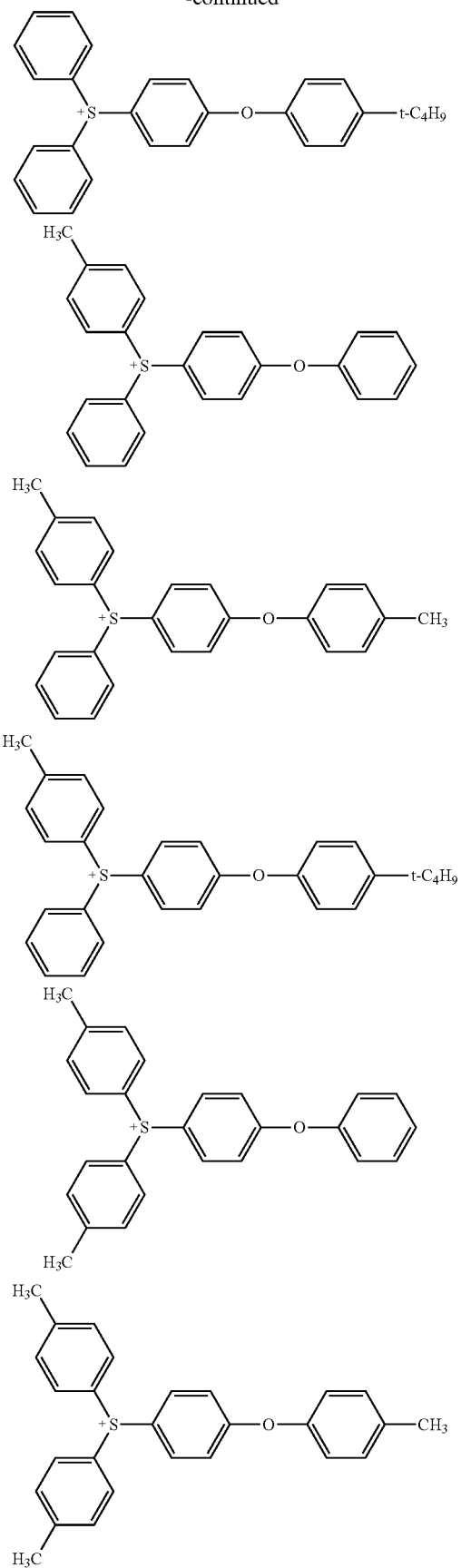
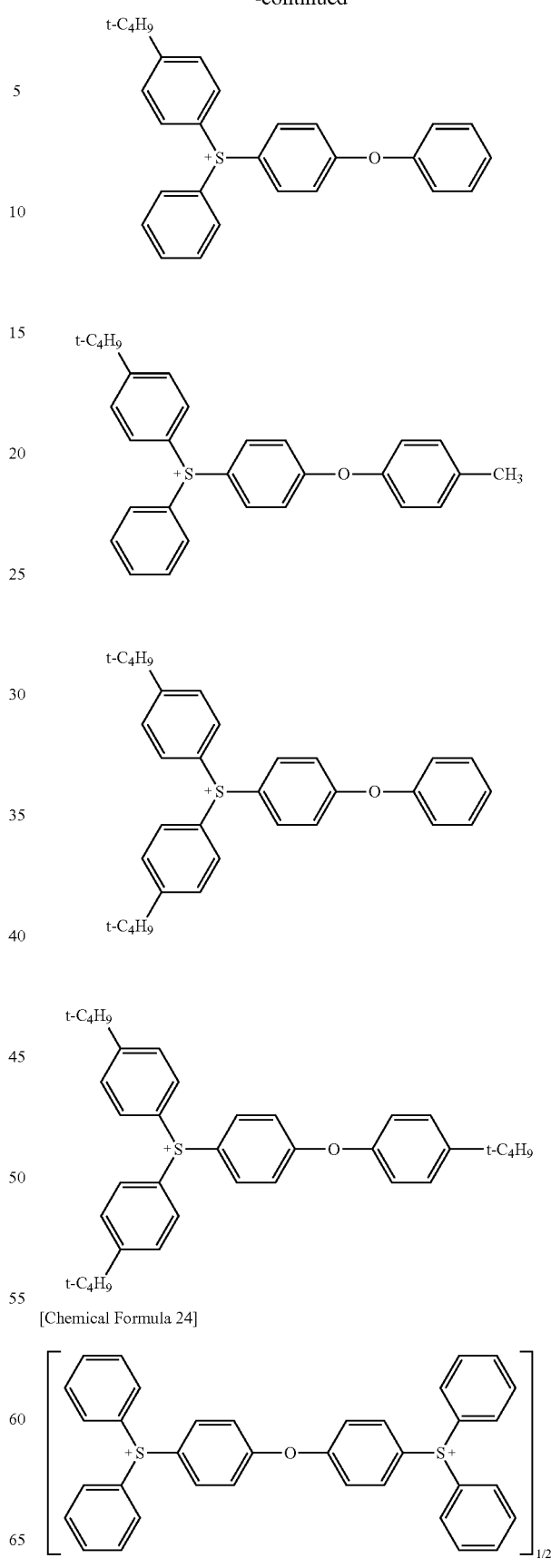
[Chemical Formula 24]

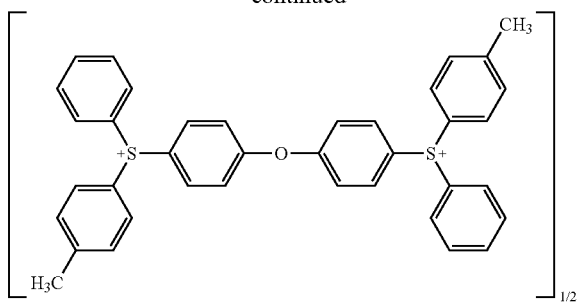
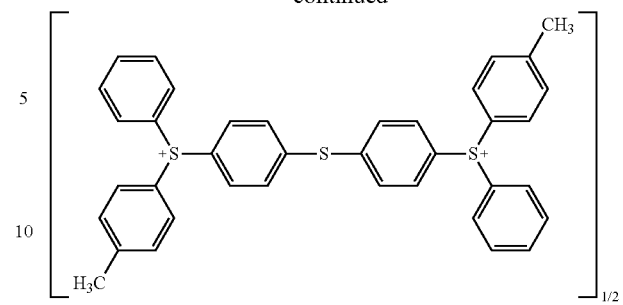
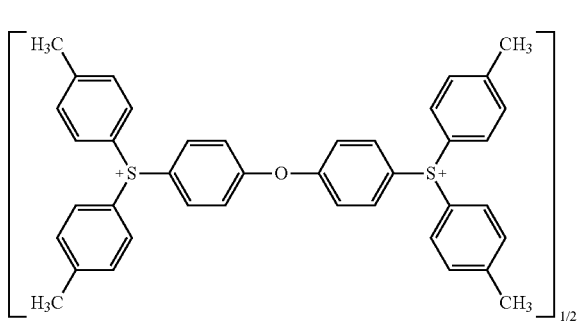
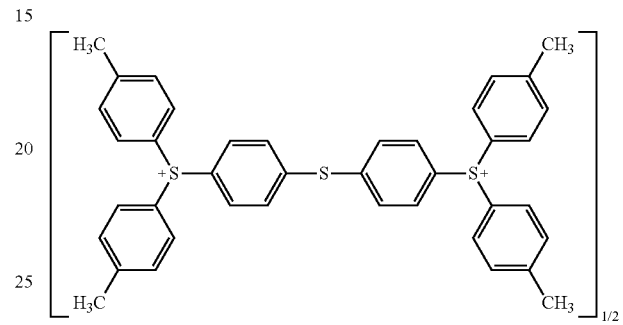
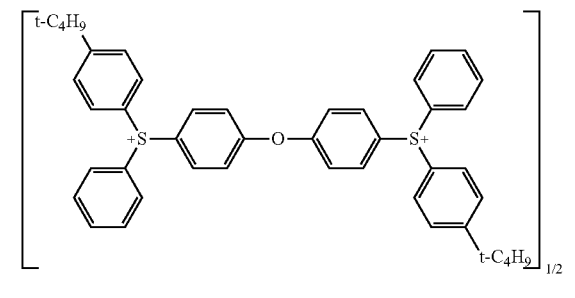
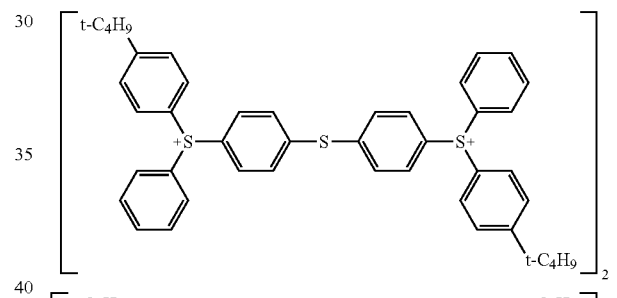
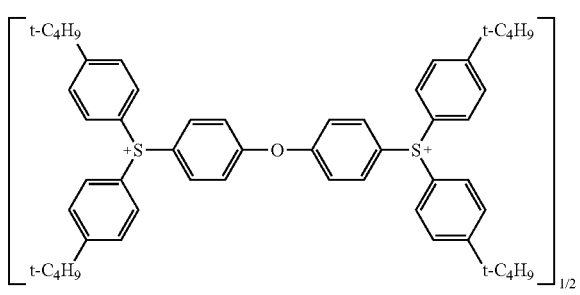
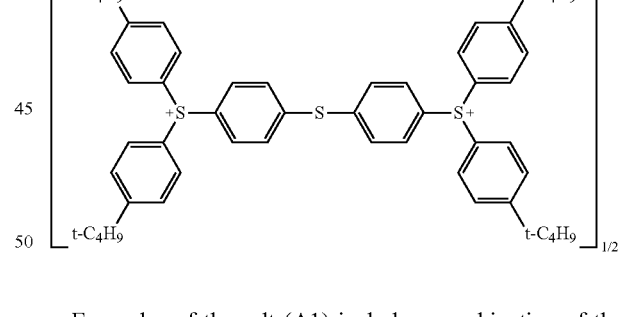

[Chemical Formula 25]

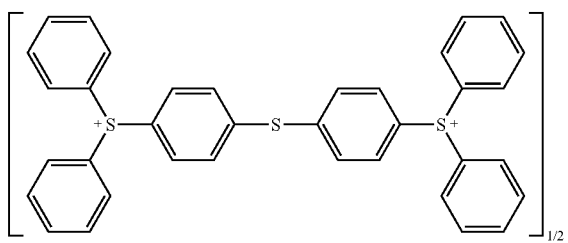

Examples of the salt (A1) include a combination of the above mentioned anion and the cation. Although any combination of the anion and the cation as described above may be employed, a combination of any one of the anions (a1-1-1), (a1-1-2), (a1-1-3), (a1-1-4), (a1-1-5), (a1-2-1), (a1-3-1), (a1-4-1) and (a1-5-1) and the cation (a2-1-1) or (a2-2) are preferable, and a combination of any one of the anions (a1-1-1) to (a1-4-1) and a triphenylsulfonium cation are more preferable.

The salt (A1) of the present invention can be produced by reactions known in the field of organic synthesis. For example, a salt (A1-I) in which $L^{a1}$ is —CO—O— can be produced by a transesterification reaction that uses an ester (A1-Ia) and an alcohol (A1-Ib) as represented in the following formula:

[Chemical Formula 26]

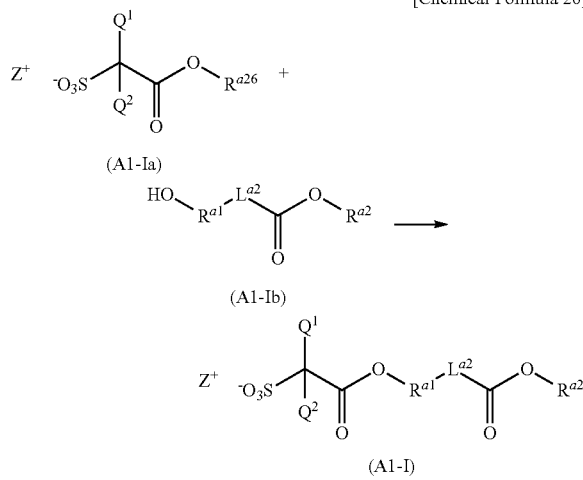

wherein the following formula: $R^{a26}$ represents a linear or a branched $C_{1-4}$ alkyl group, and preferably represents a methyl group; and other symbols are identical to those described above.

The transesterification reaction can be performed while stirring in an aprotic solvent such as dichloroethane, toluene, ethylbenzene, monochlorobenzene, acetonitrile, and N,N-dimethylformamide at a temperature ranging from about 0° C. to about 150° C. (preferably, about 50° C. to about 100° C.), in general.

For the transesterification reaction, a catalyst may be employed. Examples of the catalyst for the transesterification reaction include basic catalysts such as lithium amide ($LiNH_2$), lithium hydride, and samarium chloride. Although the basic catalyst may be excessively used, the amount of the base catalyst to be used is preferably about 0.1 mole to 2.0 moles with respect to 1 mole of the ester (A1-Ia), in general.

The salt (A1-II) in which $L^{a2}$ is —CO—O—$(CH_2)_{L1}$—, for example, is prepared by an esterification reaction employing a carboxylic acid salt (A1-IIa) and an alkyl halide (A1-IIb) as represented in the following formula:

[Chemical Formula 27]

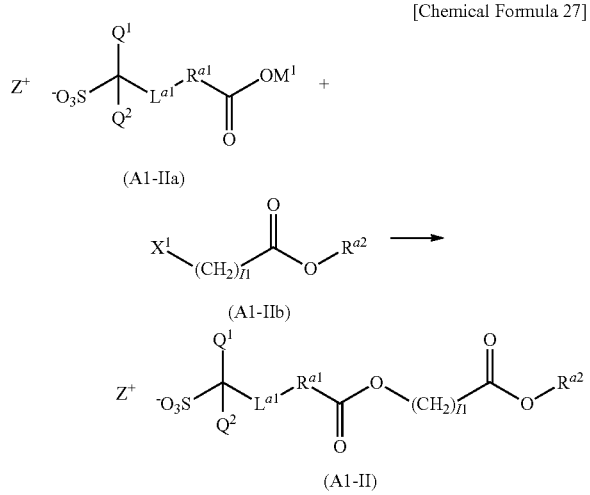

wherein the following formula, $M^1$ represents an alkali metal, $X^1$ represents a halogen atom; and other symbols are identical to those described above.

As $M^1$, Cs, K, and Na exhibiting high reactivity are preferable, and among those, K and Na which are easily availability are more preferable. From the standpoint of reactivity and easy availability, I, Br, and Cl are preferable as $X^1$. In the presence of an iodide of an alkali metal, an esterification reaction that uses alkyl bromide or alkyl chloride may be performed.

The esterification reaction employing alkyl halide is performed while stirring in an aprotic solvent such as N,N-dimethylformamide or dimethylsulfoxide at a temperature ranging from about 0° C. to about 150° C. (preferably, about 10° C. to about 100° C.), in general.

The salt (A1-III) in which $L^{a2}$ is —O—$(CH_2)_{L1}$—, for example, is prepared by an etherification reaction (Williamson ether synthesis) employing an alkoxide (A1-IIIa) and an alkyl halide (A1-IIIb) as represented in the following formula:

[Chemical Formula 28]

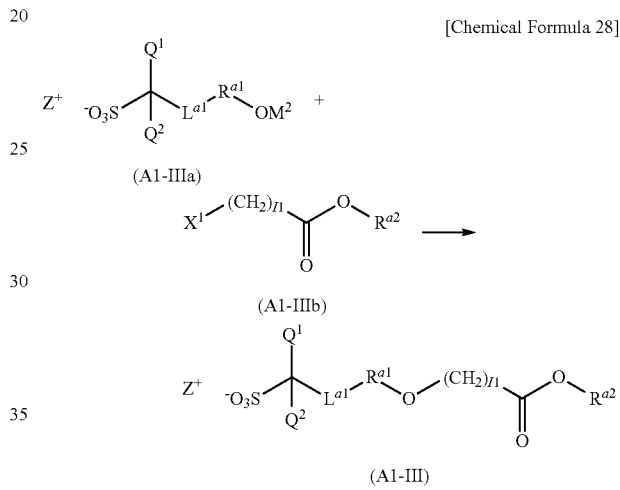

wherein $M^2$ represents an alkali metal, $X^2$ represents a halogen atom; and other symbols are identical to those described above.

Examples of $M^2$ preferably include Li, Na and K. The alkoxide (A1-IIIa) is easily prepared from a corresponding alcohol and a strong base (e.g., sodium hydride, potassium hydride, lithium hexamethyl disilazide or lithium diisopropyl amide). Examples of $X^2$ preferably include I, Br and Cl.

The etherification reaction is performed while stirring in an aprotic solvent such as chloroform, dichloroethane, toluene, ethylbenzene, monochlorobenzene, acetonitrile, and N,N-dimethylformamide at a temperature ranging from about 0° C. to about 150° C. (preferably, about 10° C. to about 80° C.), in general.

The salt (A1) of the present invention can be prepared by a cation exchange reaction employing the salt (A1a) and the salt (A1b) as represented in the following formula:

[Chemical Formula 29]

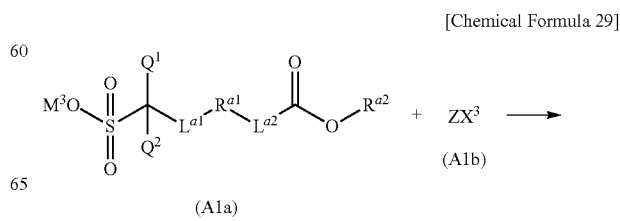

-continued

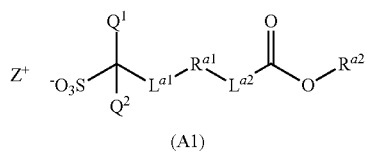

(A1)

wherein $M^3$ represents an alkali metal, and $X^3$ represents Br or I, and the same symbols as indicated above have the same corresponding meanings as indicated above.

The salt (A1a), which is a starting material of the cation exchange reaction, may be prepared by appropriately employing a well-known organic synthesis reaction, for example, the above mentioned transesterification reaction, the esterification reaction and the etherification reaction.

In general, the cation exchange reaction can be performed in an inert solvent such as chloroform, acetonitrile, water or methanol, at a temperature ranging from about 0° C. to about 150° C. (preferably, at about 0° C. to about 100° C.). The amount of the salt (A1b) to be used is about 0.5 moles to 2 moles with respect to 1 mole of the salt (A1a), in general. In the cation exchange reaction, a catalyst (e.g., silver chloride and dimethyl sulfate) may be employed.

The salt (A1) obtained can be purified through a separatory purification, water-washing, recrystallization, and the like.

The salt (A1) of the present invention is preferably used as an acid generator, especially, it is preferably used as a acid generator for a chemically amplified resist composition. By employing the salt (A1) of the present invention as the acid generator, a resist pattern excellent in a resolution and a mask error enhancement factor is obtained. The salt (A1) of the present invention may be employed alone or in combination with two or more. Further, the salt (A1) of the present invention may be used together with another acid generator, as long as the effect of the present invention is not impaired.

<Resist Composition>

The present invention provides a resist composition comprising the salt (A1) and a resin which becomes soluble in an aqueous alkali solution by the action of an acid (hereinafter, referred to as resin (B)). The content of the salt (A1) in the resist composition of the present invention is preferably 1 part by mass or more (more preferably 3 parts by mass or more), and is preferably 30 parts by mass or less (more preferably 20 parts by mass or less, even more preferably 15 parts by mass or less).

The resist composition of the present invention is useful as a chemically amplified positive type resist composition. A commonly-used chemically amplified positive type resist composition comprises a resin (B), a solvent (D) and, if necessary, a basic compound (C), other than an acid generator (A). Hereinafter, each component of the resist composition will be described below.

<Resin (B) which Becomes Alkali Soluble by the Action of the Acid>

The resin (B) is prepared by polymerizing a monomer which becomes soluble in an aqueous alkali solution by the action of an acid (hereinafter referred to as "an acid solubilization monomer (b1)". The acid solubilization monomer (b1) may be used alone or in combination with two or more. "Becoming soluble in an aqueous alkali solution by the action of an acid" means "being insoluble or poorly soluble in an aqueous alkali solution before contact with an acid, but becoming soluble in an aqueous alkali solution after contact with the acid".

An acid solubilization monomer (b1) includes monomers containing an acid-labile group. Here, an "acid-labile group" means a group that forms a hydrophilic group (e.g., hydroxyl group or carboxyl group) as a result of a cleaving off a leaving group upon making contact with an acid. Examples of the acid-labile group include an alkoxycarbonyl group (i.e., an ester bond containing a tertiary alcohol residue) represented by the following formula (III) in which an oxy group (—O—) is bonded to a tertiary carbon atom (excluding a bridgehead carbon atom in a bridged cyclic hydrocarbon group).

[Chemical Formula 30]

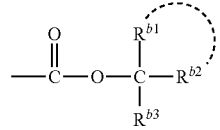

(III)

In the formula (III), $R^{b1}$ to $R^{b3}$ each independently represent a linear or branched aliphatic hydrocarbon group, or $R^{b1}$ and $R^{b2}$ may be bonded to each other such that a ring is formed.

Examples of the acid-labile group (III) includes a 1,1-dialkylalkoxycarbonyl group (in the formula (III), $R^{b1}$ to $R^{b3}$ are an alkyl group, preferably a tert-butoxy carbonyl group), a 2-alkyl-2-adamantyloxycarbonyl group (in the formula (III), $R^{b1}$, $R^{b2}$ and the carbon atom are bonded each other to form an adamantyl group, and $R^{b3}$ represents an alkyl group), and a 1-(1-adamantyl)-1-alkoxycarbonyl group (in the formula (III), $R^{b1}$ and $R^{b2}$ are a alkyl group, $R^{b3}$ is an adamantyl group).

Examples of the acid solubilization monomer (b1) preferably include a monomer having the acid labile group (III) and an olefinic double bond, more preferably a (meth)acrylate ester, a norbornene carboxylate ester, a tricyclodecen carboxylate ester or a tetracyclodecen carboxylate ester, all of which have the acid labile group (III). In the description of the present invention, "(meth)acrylate" is a generic term for "acrylates and methacrylates", and similarly, other description containing "(meth)acryl" has the same meaning as described above.

The resolution of the resist can be enhanced if a resin obtained by polymerizing an acid solubilization monomer (b1) having a bulky structure such as a cyclic aliphatic hydrocarbon group (e.g., cyclohexane ring, adamantane ring, or norbornane ring) is used. Monomers represented by formulae (b1-1), (b1-2), and (b1-3) are preferable as the acid solubilization monomer having such a bulky structure. Furthermore, the acid solubilization monomer (b1-3) containing a norbornene ring has, not only an effect of enhancing the resolution of the resist, but also an effect of enhancing dry etch resistance of the resist by incorporating a rigid norbornane ring into the main chain of a resin.

[Chemical Formula 31]

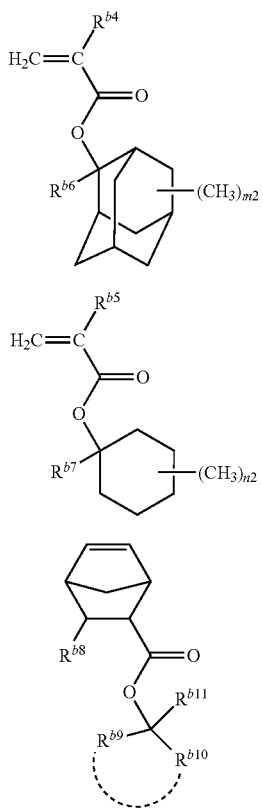

In the formulae (b1-1) and (b1-2), $R^{b4}$ and $R^{b5}$ each independently represent a hydrogen atom, a halogen atom, or a methyl group, and are preferably a methyl group.

In the formulae (b1-1) and (b1-2), $R^{b6}$ and $R^{b7}$ each independently represent a linear, branched or cyclic $C_{1-10}$ aliphatic hydrocarbon group (preferably a linear or branched $C_{1-8}$ aliphatic hydrocarbon group). The number of carbon atoms in the aliphatic hydrocarbon group of each of $R^{b6}$ and $R^{b7}$ is preferably 8 or less, and is more preferably 6 or less. Examples of the aliphatic hydrocarbon group include chain aliphatic hydrocarbon groups such as a methyl group, an ethyl group, a 1-methylethyl group (an isopropyl group), a 1,1-dimethylethyl group (a tert-butyl group), a 2,2-dimethylethyl group, a propyl group, a 1-methylpropyl group, a 2,2-dimethylpropyl group, a 1-ethylpropyl group, a butyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group, and an octyl group; and cyclic aliphatic hydrocarbon groups such as a cycloheptyl group, a methylcycloheptyl group, a cyclohexyl group, a methylcyclohexyl group, a dimethylcyclohexyl group, a norbornyl group, and a methylnorbornyl group.

In the formulae (b1-1) and (b1-2), m2 represents an integer ranging from 0 to 14, and n2 represents an integer ranging from 0 to 10. When m2 or n2 is 0, it means that the corresponding methyl group is absent. Preferably, "m2" and "n2" each independently represent an integer ranging from 0 to 3, and more preferably is 0 or 1.

In the formula (b1-3), $R^{b8}$ represents a hydrogen atom, a $C_{1-3}$ alkyl group, a carboxyl group, a cyano group, or an alkoxycarbonyl group (—$COOR^{b12}$), at least one hydrogen atom of the alkyl group may be replaced with a hydroxyl group and the like. $R^{b12}$ represents a linear, branched or cyclic $C_{1-8}$ aliphatic hydrocarbon group, and at least one hydrogen atom of the aliphatic hydrocarbon group may be replaced with a hydroxyl group, a methylene group of the aliphatic hydrocarbon group may be replaced with an oxygen atom or a carbonyl group. Examples of the aliphatic hydrocarbon group of $R^{b8}$ which may have a substituent include a methyl group, an ethyl group, a propyl group, a hydroxymethyl group, a 2-hydroxyethyl group. Examples of $R^{b12}$ include a methyl group, an ethyl group, a propyl group, a 2-oxo-oxolan-3-yl group, and a 2-oxo-oxolan-4-yl group.

In the formula (b1-3), $R^{b9}$ to $R^{b11}$ each independently represent a linear, branched or cyclic $C_{1-12}$ aliphatic hydrocarbon group, or $R^{b9}$ and $R^{b11}$ may be bonded each other such that a ring is formed, at least one hydrogen atom of the aliphatic hydrocarbon group may be replaced with a hydroxyl group, a methylene group of the aliphatic hydrocarbon group may be replaced with an oxygen atom or a carbonyl group.

Examples of the acid solubilization monomer (b1-1) having an adamantyl group include 2-methyl-2-adamantyl (meth)acrylate, 2-ethyl-2-adamantyl (meth)acrylate, 2-isopropyl-2-adamantyl (meth)acrylate, 2-butyl-2-adamantyl (meth)acrylate, 2-methyl-2-adamantyl-α-chloroacrylate, and 2-ethyl-2-adamantyl-α-chloroacrylate. Among them, 2-ethyl-2-adamantyl (meth)acrylate, 2-isopropyl-2-adamantyl (meth)acrylate are preferable because these monomers provides a resin excellent in sensitivity and thermal resistance, and a methacrylate-type is more preferable.

As the acid solubilization monomer (b1-2) having a cyclohexyl group, 1-ethyl-1-cyclohexyl (meth)acrylate is preferable, and 1-ethyl-1-cyclohexyl methacrylate is more preferable Examples of the acid solubilization monomer (b1-3) having a norbornene ring include t-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate, and 1-(1-adamantyl)-1-methylethyl 5-norbornene-2-carboxylate.

Among the acid solubilization monomers (b1-1) to (b1-3), the acid solubilization monomer (b1-1) having an adamantyl group is preferable. By employing the acid solubilization monomer (b1-1), it is likely to be obtained a resist composition excellent in a resolution property. The acid solubilization monomer (b1-1), in which $R^{b6}$ is an alkyl group, is prepared by a reaction between 2-alkyl-2-adamantanole or a metal salt thereof with a (meth)acrylate halide, in general.

The resin (B) is preferably a copolymer obtained by polymerizing the acid solubilization monomer (b1) and other monomer which does not have an acid labile group. When the resin (B) is a copolymer, an amount of the structural unit derived from the acid solubilization monomer (b1) is preferably 10 mole % to 80 mole % based on 100 mole % of the total structural unit. Further, the amount of a structural unit derived from the acid solubilization monomer having an adamantyl group (especially, the acid solubilization monomer (b1-1)) is preferable to be 15 mole % or more based on 100 mole % of the acid solubilization monomer (b1). When the content ratio of the acid solubilization monomer having the adamantyl group increases, a dry etch resistance of the resist is improved.

Examples of the other monomer include esters (meth) acrylic acid, (meth)acrylonitriles, norbornenes, hydroxystyrenes, aliphatic unsaturated dicarboxylic acid anhydrides (e.g., maleic acid anhydride) and a itaconic acid anhydride, all of which have no acid labile group.

A resolution of the resist and an adhesion of the resist to a substrate can be enhanced, when a monomer containing a hydroxyl group (hereinafter, may be referred to simply as a "hydroxyl group containing monomer (b2)") such as hydroxystyrenes (e.g., p-hydroxystyrene or m-hydroxystyrene) is used as the other monomer. Furthermore, a hydroxyl group may be formed in a resin by using acetoxystyrenes as the other monomer and performing a deacetylation with an acid after polymerization.

When the resist composition is used in a KrF excimer laser exposure (248 nm), a sufficient transmittance can be obtained even if hydroxystyrenes are used as the hydroxyl group containing monomer (b2). However, when using an ArF excimer laser exposure (193 nm) or the like with a shorter wavelength, a monomer represented by formula (b2-1) is preferably used as the hydroxyl group containing monomer (b2). A single type of a hydroxyl group-containing monomer (b2-1) having an adamantyl group may be used alone, or in combination with two or more types of them.

[Chemical Formula 32]

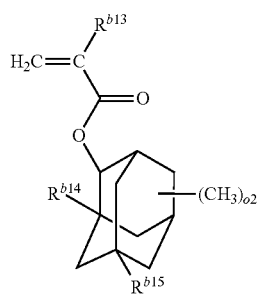
(b2-1)

In Formula (b2-1), $R^{b13}$ represents a hydrogen atom or a methyl group, and is more preferably a methyl group. $R^{b14}$ and $R^{b15}$ each independently represent a hydrogen atom, a methyl group, or a hydroxyl group. "o2" represents an integer ranging from 0 to 10 (preferably an integer ranging from 0 to 3, and more preferably 0 or 1). When o2 is 0, it means that the corresponding methyl group is absent.

Examples of the hydroxyl group-containing monomer (b2-1) having an adamantyl group preferably include 3-hydroxy-1-adamantyl (meth)acrylate and 3,5-dihydroxy-1-adamantyl (meth)acrylate, 3-hydroxy-1-adamantyl (meth)acrylate is more preferable, and 3-hydroxy-1-adamantyl methacrylate is even more preferable. The hydroxyl group-containing monomer (b2-1) is prepared by reacting the corresponding hydroxy adamantane with (meth)acrylic acid. Further, 3-hydroxy-1-adamantyl (meth)acrylate and 3,5-dihydroxy-1-adamantyl (meth)acrylate are commercially available.

By employing a monomer having a lactone ring (hereinafter referred to as "lactone ring-containing monomer (b3)"), resolution and adhesion to a substrate are improved in a similar manner of the hydroxyl group-containing monomer's case. Examples of the lactone ring include single rings such as a β-propiolactone ring, a γ-butyrolactone ring, and a δ-valerolactone ring; and condensed rings which are obtained by condensation of a lactone ring that is a single ring, with another ring. Preferred examples of the lactone ring include a γ-butyrolactone ring, and condensed rings which are obtained by condensation of a γ-butyrolactone ring with another ring.

Preferred examples of the lactone ring-containing monomer (b3) is a monomer represented by the following formulae (b3-1), (b3-2) or (b3-3), these monomers may be used alone or in combination with two or more.

[Chemical Formula 33]

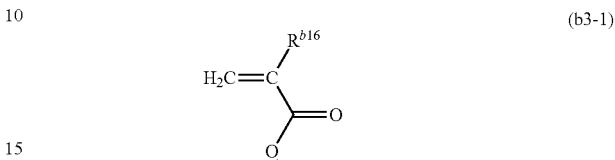
(b3-1)

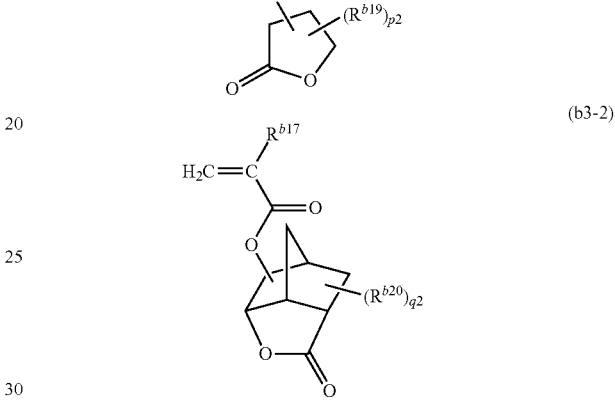
(b3-2)

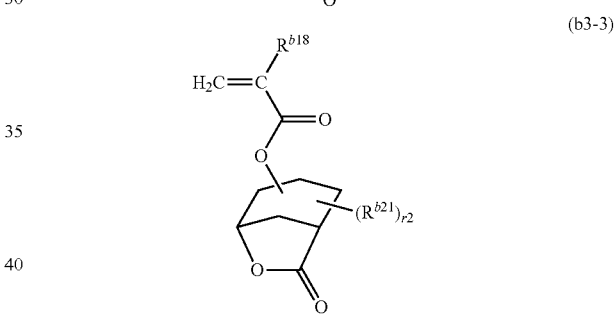
(b3-3)

In the formulae (b3-1) to (b3-3), $R^{b16}$ to $R^{b18}$ each independently represent a hydrogen atom or a methyl group, and a methyl group is preferable. $R^{a19}$ to $R^{b21}$ each independently represent a methyl group, a trifluoro methyl group or a halogen atom. "p2" to "r2" each independently represent an integer ranging from 0 to 3. When any of p2 to r2 is 0, it means that any of $R^{b19}$ to $R^{b21}$ is absent. When any of p2 to r2 is not less than 2, it means that a plurality of $R^{b19}$ to $R^{b21}$ may be the same or different from each other.

In the formula (b3-1), a preferable position in which the (meth)acryloyloxy group is bonding to is α, or β-position of the γ-lactone ring, α-position of the γ-lactone ring is more preferable. In the formula (b3-2), a preferable position in which the (meth)acryloyloxy group is bonding to is 2- or 3-position of a 5-oxo-4-oxatricyclo[4.2.1.0$^{3,7}$]nonane ring. In the formula (b3-3), a preferable position in which the (meth)acryloyloxy group is bonding to is 4-position of a 7-oxo-6-oxabicyclo[3.2.1]octane ring.

Examples of the lactone ring-containing monomer (b3-1) include α-(meth)acryloyloxy-γ-butyrolactone, α-(meth) acryloyloxy-β, β-dimethyl-γ-butyrolactone, β-(meth)acryloyloxy-γ-butyrolactone, β-(meth)acryloyloxy-α-methyl-γ-butyrolactone. Among them, α-(meth)acryloyloxy-γ-butyrolactone (i.e., tetrahydro-2-oxo-3-furyl (meth)acrylate) is more preferable.

Examples of the lactone ring-containing monomer (b3-2) having a condensed lactone ring are represented by the following formulae:

[Chemical Formula 34]

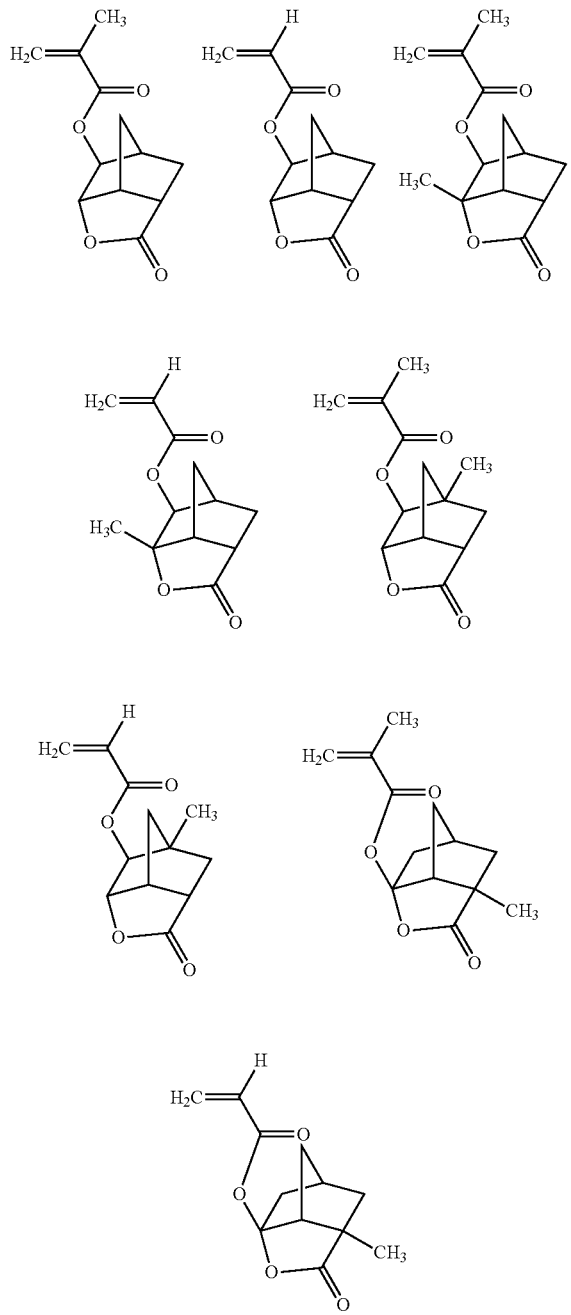

Among them, 5-oxo-4-oxatricyclo[4.2.1.0$^{3,7}$]nonan-2-yl (meth)acrylate is preferable.

Examples of the lactone ring-containing monomer (b3-3) having a condensed lactone ring are represented by the following formula:

[Chemical Formula 35]

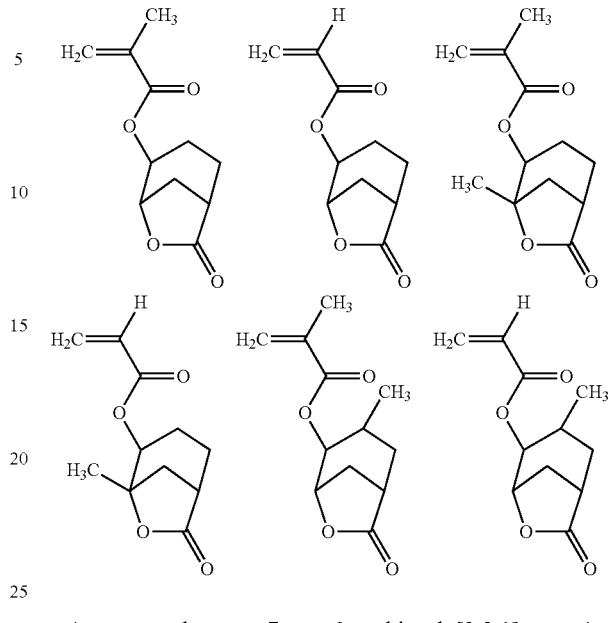

Among them, 7-oxo-6-oxabicyclo[3.2.1]octan-4-yl (meth)acrylate is preferable.

The lactone ring-containing monomer (b3-1) having γ-lactone ring is prepared by reacting a alkali metal salt of (meth)acrylic acid with a γ-butyrolactone compound containing a halogen atom (preferably bromine atom); or by reacting a (meth)acrylic acid halide, a (meth)acrylic acid or a (meth)acrylate ester with a γ-butyrolactone compound containing a hydroxyl group. The lactone ring-containing monomers (b3-2) and (b3-3) having a condensed lactone ring are prepared by reacting a (meth)acrylic acid with condensed lactones containing a hydroxyl group represented the following formulae (cf. Japanese unexamined patent application No. 2000-26446):

[Chemical Formula 36]

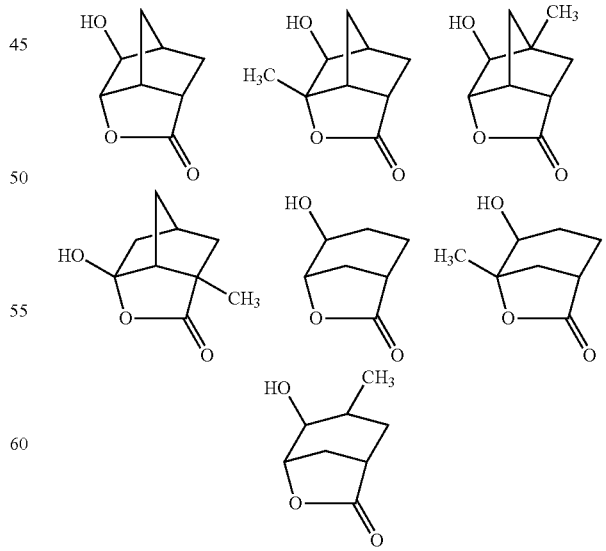

The other monomer that does not contain an acid-labile group includes a monomer containing a norbornene ring represented by the following formula (b4-1). As described above, a monomer containing a norbornene ring can enhance dry etch resistance of the resist by an incorporation of a rigid norbornane ring into the main chain of a resin.

[Chemical Formula 37]

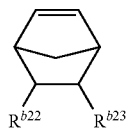

(b4-1)

In formula (b4-1), $R^{b22}$ and $R^{b23}$ each independently represent a hydrogen atom, a $C_{1-3}$ alkyl group, a carboxyl group, a cyano group, or an alkoxycarbonyl group (—$COOR^{b24}$), $R^{b22}$ and $R^{b23}$ may be bonded each other such that a carbonyloxycarbonyl group or —CO—O—CO— is formed, and at least one hydrogen atom of the alkyl group may be replaced with a hydroxyl group. $R^{b24}$ represents a linear, branched or cyclic $C_{1-8}$ aliphatic hydrocarbon group, and at least one hydrogen atom of the aliphatic hydrocarbon group may be replaced with a hydroxyl group, a methylene group contained in the aliphatic hydrocarbon group may be replaced with an oxygen atom or a carbonyl group. However, $R^{b24}$ containing an oxy group (—O—) bonded to a tertiary carbon atom is excluded. Specific examples of $R^{b24}$ and the aliphatic hydrocarbon group $R^{b22}$ and $R^{b23}$ include the same as those of the acid solubilization monomer (b1-3) having a norbornene ring.

Examples of the monomer (b4-1) having norbornene ring include 2-norbornene, 2-hydroxy-5-norbornene, 5-norbornene-2-carboxylic acid, methyl 5-norbornene-2-carboxylate, 2-hydroxy-1-ethyl 5-norbornene-2-carboxylate, 5-norbornene-2-methanol, and 5-norbornene-2,3-dicarboxylic acid anhydride.

The preferable resin (B) is a copolymer obtained by polymerizing a monomer mixture comprising at least the acid solubilization monomer (b1) {preferably the acid solubilization monomer (b1-1) having an adamantyl group}, the hydroxyl group-containing monomer (b2) {preferably the hydroxyl group-containing monomer (b2-1) having an adamantyl group} and the lactone ring containing monomer (b3) {preferably the lactone ring containing monomer (b3-1) having a γ-lactone ring}.

The weight-average molecular weight of the resin (B) is preferably 2,500 or more (more preferably 3,000 or more), and is preferably 100,000 or less (more preferably 50,000 or less, even more preferably 20,000 or less).

The method for producing the resin (B) is not particularly limited, and polymerization methods and conditions that are known in the art may be appropriately adopted for producing the resin (B). However, if a monomer containing an olefinic double bond within a cyclic aliphatic hydrocarbon group (e.g., the acid solubilization monomer (b1-3) having a norbornene ring) is to be used, it is preferable to use the monomer in an amount that is excessive with respect to a predicted amount of structural units of the monomer in a resin, since the polymerizability of the monomer is low.

<Basic Compound (C)>

A basic compound (C) may be added as a quencher to the resist composition of the present invention. For example, performance deterioration of a resist film caused by inactivation of acid which occurs due to post exposure delay can be diminished by the use of the basic compound (C). When the basic compound (C) is used, the amount of the basic compound (C) is preferably 0.01 parts by mass or more (more preferably 0.05 parts by mass or more, and even more preferably 0.1 parts by mass or), per 100 parts by mass of the resin (A), and is preferably 5 parts by mass or less (more preferably 3 parts by mass or less, and even more preferably 2 parts by mass or less), per 100 parts by mass of the resin (B).

As the basic compound (C), a nitrogen-containing basic compound is preferable. Examples of the nitrogen-containing basic compound (C) include an amine and an ammonium hydroxide. The amine may be an aliphatic amine or an aromatic amine. As the aliphatic amine, any one of a primary amine, secondary amine, or tertiary amine may be used. The aromatic amine may be either an amine, such as aniline, in which an amino group is bonded to an aromatic ring, or a heteroaromatic amine such as pyridine. The nitrogen-containing basic compound (C) is preferably an aromatic amine represented by the following formula (C1), and aniline represented by the formula (C1-1) is particularly preferable.

[Chemical Formula 38]

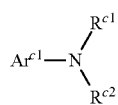

(C1)

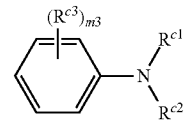

(C1-1)

In formula (C1), $Ar^{c1}$ represents a $C_{6-20}$ aromatic hydrocarbon group. $R^{c1}$ and $R^{c2}$ each independently represent a hydrogen atom, a linear or branched $C_{1-6}$ aliphatic hydrocarbon group, a cyclic $C_{5-10}$ aliphatic hydrocarbon group, or a $C_{6-20}$ aromatic hydrocarbon group. The aliphatic hydrocarbon groups and the aromatic hydrocarbon group may be each independently substituted with a hydroxyl group, an amino group, or a linear or branched $C_{1-6}$ alkoxy group. Further, the aliphatic hydrocarbon groups may be substituted with a $C_{6-20}$ aromatic hydrocarbon group, and the aromatic hydrocarbon group may be substituted with a linear or branched $C_{1-6}$ aliphatic hydrocarbon group, or a cyclic $C_{5-10}$ aliphatic hydrocarbon group. Further, the alkoxy group may be substituted with a hydroxyl group, an amino group, or a linear or branched $C_{1-6}$ alkoxy group, and the amino group may be substituted with a $C_{1-4}$ aliphatic hydrocarbon group.

In formula (C1-1), $R^{c1}$ and $R^{c2}$ are the same as described above. $R^{c3}$ represents a linear or branched $C_{1-6}$ aliphatic hydrocarbon group, a cyclic $C_{5-10}$ aliphatic hydrocarbon group, a linear or branched $C_{1-6}$ alkoxy group, or a $C_{6-20}$ aromatic hydrocarbon group. The aliphatic hydrocarbon groups, the alkoxy group, and the aromatic hydrocarbon group may each independently have a substituent as described for formula (C1). "m3" represents an integer ranging from 0 to 3. When m3 is 0, it means that $R^{c3}$ is absent. When "m3" is not less than 2, the plurality of $R^{c3}$ may be the same or different from each other.

Examples of the aromatic amine (C1) include 1-naphthylamine, and 2-naphthylamine. Examples of the aniline (C1-1) include aniline, diisopropyl aniline, 2-, 3- or 4-methylaniline, 4-nitroaniline, N-methylaniline, N,N-dimethylaniline, and diphenylamine. Among them, diisopropyl aniline (particularly, 2,6-diisopropyl aniline) is preferable.

A quaternary ammonium hydroxide represented by the following formula (C2) is also preferable as the nitrogen-containing basic compound (C).

[Chemical Formula 39]

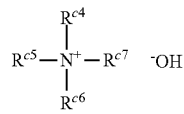
(C2)

In formula (C2), $R^{c4}$ to $R^{c6}$ each independently represent a hydrogen atom, a linear or branched $C_{1-6}$ aliphatic hydrocarbon group, a cyclic $C_{5-10}$ aliphatic hydrocarbon group, or a $C_{6-20}$ aromatic hydrocarbon group. $R^{c7}$ represents a linear or branched $C_{1-6}$ aliphatic hydrocarbon group, or a cyclic $C_{5-10}$ aliphatic hydrocarbon group. The aliphatic hydrocarbon groups and the aromatic hydrocarbon group may each independently have a substituent as described for formula (C1).

Examples of the quaternary ammonium hydroxide (C2) include tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-(trifluoromethyl)phenyltrimethylammonium hydroxide, and (2-hydroxyethyl)trimethylammonium hydroxide.

Other examples of the nitrogen-containing basic compound (C) include compounds represented by formulae (C3) to (C11).

[Chemical Formula 40]

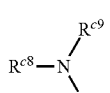
(C3)

(C4)

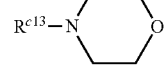
(C5)

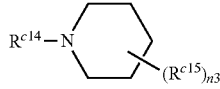
(C6)

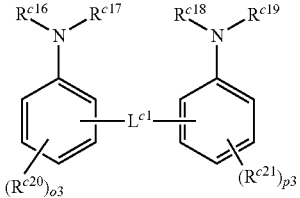
(C7)

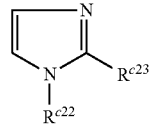
(C8)

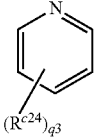
(C9)

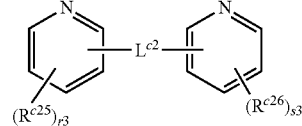
(C10)

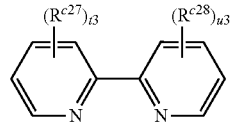
(C11)

In formula (C3), $R^{c8}$ represents a linear or branched $C_{1-6}$ aliphatic hydrocarbon group, or a cyclic $C_{5-10}$ aliphatic hydrocarbon group. $R^{c9}$ and $R^{c10}$ each independently represent a hydrogen atom, a linear or branched $C_{1-6}$ aliphatic hydrocarbon group, or a cyclic $C_{5-10}$ aliphatic hydrocarbon group. In formulae (C4) to (C8), $R^{c11}$ to $R^{c14}$, $R^{c16}$ to $R^{c19}$, and $R^{c22}$, each of which is bonded to a nitrogen atom, each independently represent a hydrogen atom, a linear or branched $C_{1-6}$ aliphatic hydrocarbon group, a cyclic $C_{5-10}$ aliphatic hydrocarbon group, or a $C_{6-20}$ aromatic hydrocarbon group. In formula (C6), $R^{c15}$ represents a linear or branched $C_{1-6}$ aliphatic hydrocarbon group, a cyclic $C_{3-6}$ aliphatic hydrocarbon group, or a $C_{2-6}$ alkanoyl group, and n3 represents an integer ranging from 0 to 8. When n3 is 0, it means that $R^{c15}$ is absent. When n3 is not less than 2, a plurality of $R^{c15}$ may be the same or different from each other. In formula (C8), $R^{c23}$, which is bonded to an aromatic carbon, represents a hydrogen atom, a linear or branched $C_{1-6}$ aliphatic hydrocarbon group, a cyclic $C_{5-10}$ aliphatic hydrocarbon group, a linear or branched $C_{1-6}$ alkoxy group, or a $C_{6-20}$ aromatic hydrocarbon group. In formula (C7), and formulae (C9) to (C11), $R^{c20}$, $R^{c21}$, and $R^{c24}$ to $R^{c28}$, each of which is bonded to an aromatic carbon, each independently represent a linear or branched $C_{1-6}$ aliphatic hydrocarbon group, a cyclic $C_{5-10}$ aliphatic hydrocarbon group, a linear or branched $C_{1-6}$ alkoxy group, or a $C_{6-20}$ aromatic hydrocarbon group, and o3 to u3 each independently represent an integer ranging from 0 to 3. When any of o3 to u3 are 0, it means that the corresponding substituent does not exist. When any of o3 to u3 are not less than 2, it means that a plurality of $R^{c20}$ to $R^{c28}$, respectively, may be the same or different from each other. In formulae (C7) and (C10), $L^{c1}$ and $L^{c2}$ each independently represent a $C_{2-6}$ divalent aliphatic hydrocarbon group (preferably $C_{2-6}$ alkylene group), a carbonyl group (—CO—), —N($R^{c29}$)—, a thio group (—S—), a dithio group (—S—S—), or a combination thereof. $R^{c29}$ represents a hydrogen atom, or a linear or branched $C_{1-6}$ aliphatic hydrocarbon group. Further, in formulae (C3) to (C11), the aliphatic hydrocarbon groups, the alkoxy group, and the aromatic hydrocarbon group may each independently have a substituent as described for formula (C1).

Examples of the compound (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, and 4,4'-diamino-3,3'-diethyldiphenylmethane.

The compound (C4) is, for example, piperazine. The compound (C5) is, for example, morpholine. Examples of the compound (C6) include piperidine, and a hindered amine compound having a piperidine skeleton as disclosed in Japanese Laid-Open Patent Publication No. 11-52575. The compound (C7) is, for example, 2,2'-methylenebisaniline.

Examples of the compound (C8) include imidazole, and 4-methylimidazole. Examples of the compound (C9) include pyridine, and 4-methylpyridine and the like. Examples of the compound (C10) include 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, and 2,2'-dipicolylamine. The compound (C11) is, for example, bipyridine.

<Solvent (D)>

Examples of the solvent (D) include, for examples, glycol ether esters such as ethyl cellosolve acetate, methyl cellosolve acetate, and propylene glycol monomethyl ether acetate; glycol ethers such as propylene glycol monomethyl ether; esters such as ethyl lactate, butyl acetate, amyl acetate, and ethyl pyruvate; and ketones such as acetone, methylisobutylketone, 2-heptanone, and cyclohexanone; and cyclic esters such as γ-butyrolactone. The above mentioned solvent (D) may be used alone or in the combination with two or more.

The content of the solvent (D) in the entire resist composition is 50% by mass or more (preferably 70% by mass or more, and more preferably 90% by mass or more), and is 99% by mass or less (preferably 97% by mass or less), in general.

<Optionally Selected Component (E)>

The resist composition of the present invention may contain any optionally selected component (E) as necessary. The optionally selected component (E) is not limited to any specific component. An additive such as a sensitizer, a dissolution inhibitor, another resin, a surfactant, a stabilizer, and a dye, which is known in this technical field, may be used.

<Method for Producing Resist Pattern>

In general, a resist pattern is formed by a method including:

(1) a step of coating a resist composition on a substrate to obtain a resist film (hereinafter referred to as "coating step 1");

(2) a step of pre-baking the resist film (hereinafter referred to as "pre-baking step 2");

(3) a step of exposing the pre-baked resist film (hereinafter referred to as "exposure step 3");

(4) a step of subjecting the exposed resist film to post-exposure-baking (hereinafter referred to as "post-exposure-baking step 4"); and (5) a step of developing, by using an alkaline liquid developer, the resist film having been subjected to the post-exposure-baking, to form a resist pattern (hereinafter referred to as "development step 5"). Hereinafter, the steps will be described in order, respectively.

<Coating Step 1>

Prior to coating of the resist composition on a substrate, it is desirable that each component of the resist composition is previously blended with each other in a solvent, and is then filtered through a filter having a pore size of about 0.2 μm or less. This filtration improves a uniformity of a coated film (resist film).

A substrate to which the resist composition is coated may be selected in accordance with a usage as necessary. For example, a silicon wafer and a quartz wafer having a sensor, a circuit, a transistor, and the like formed thereon are exemplified as the substrate.

A method for applying the resist composition to form a coating film on the substrate is not limited to any specific method. A usual coating method such as a spin coating method can be employed as necessary.

<Pre-Baking Step 2>

Through pre-baking, a mechanical strength of a resist film can be enhanced, and a diffusion degree of active species (H$^+$) in an exposed resist film can be adjusted. The pre-baking temperature $T_{PB}$ is, for example, about 50° C. to about 200° C.

<Exposure Step 3>

The pre-baked resist film is exposed by use of a mask corresponding to an intended pattern (for example, contact holes). The exposure may be either a dry exposure or an immersion exposure. As an exposure apparatus, for example, a reduction projection exposure apparatus is used. Various light sources can be used as an exposure light source, and examples of the exposure light source include: light sources, such as a KrF excimer laser (wavelength 248 nm), an ArF excimer laser (wavelength 193 nm), and an $F_2$ laser (wavelength 157 nm), for emitting ultraviolet laser light; and light sources for emitting harmonic far-ultraviolet laser light or harmonic vacuum ultraviolet laser light which is wavelength-converted from a laser light emitted by a solid-state laser light source (such as a YAG or semiconductor laser). The exposure amount may be determined as necessary in accordance with kinds and the contents of the components of the resist composition to be used.

<Post-Exposure-Baking Step 4>

The post-exposure-baking is conducted in order to promote diffusion of active species (H$^+$) and a reaction of the active species in the exposed resist film. The post-exposure-baking temperature $T_{PEB}$ is about 50° C. to about 200° C., and is preferably about 70° C. to about 150° C., in general.

<Development Step 5>

The development is performed by means of a development apparatus by contacting the substrate having the resist film formed thereon with a usual liquid developer. Examples of the liquid developer include basic aqueous solutions (specifically, an aqueous solution of tetramethylammonium hydroxide, an aqueous solution of (2-hydroxyethyl)trimethylammonium hydroxide (generally referred to as choline), or the like). A surfactant may be added to the liquid developer as necessary. It is preferable that the resist pattern is formed by draining off the liquid developer, water-washing, and removing the water.

EXAMPLE

Hereinafter, the present invention will be described more specifically by way of examples, which are not construed to limit the scope of the present invention, and various modifications can be made within the range of the gist described above and below, which modifications are encompassed in the technical scope of the present invention.

The "%" and "part(s)" used to represent the content and the amount of any component in the following descriptions are on a mass basis unless otherwise specifically noted.

Structures of compounds were determined by NMR (EX-270 Type, manufactured by JEOL Ltd.) and mass spectrometry (LC: 1100 Type, manufactured by AGILENT TECHNOLOGIES LTD., MASS: LC/MSD Type or LC/MSD TOF Type, manufactured by AGILENT TECHNOLOGIES LTD.).

The weight-average molecular weight of the resin is a value measured by gel permeation chromatography.

Apparatus: HLC-8120GPC Type (manufactured by TOSOH CORPORATION)

Column: "TSKgel Multipore $H_{XL}$-M" three-connected columns and guard column (manufactured by TOSOH CORPORATION)

Eluant: tetrahydrofuran

Flow rate: 1.0 mL/min.

Detector: RI detector

Column temperature: 40° C.

Injection rate: 100 μL

1. Synthesis of Acid Generator (1) Synthesis of Salt (A1-1-1)

In a reaction container, 10.00 parts of a salt (A1-1-1a) was added to 80.00 parts of chloroform, and stirred until the salt was dissolved. To this solution, 7.97 parts of a compound (A1-1-1b) (97.1% purity) was added, followed by adding 0.15 parts of lithium amide (LiNH$_2$), and stirred for 30 minutes at 23° C. Then, 13.00 parts of molecular sieve (Molecular Sieves 5A; manufactured by Wako Pure Chemical Industries, Ltd.) was added, and the mixture was stirred at 60° C. for 8 hours. The resulting mixture was then cooled to 23° C., and filtered to obtain a filtrate. The filtrate was mixed with 24.53 parts of ion exchanged water and then stirred. Next, the organic layer was separated and recovered. A water-rinsing manipulation was conducted twice on the recovered organic layer. To the water-rinsed organic layer, 1.33 parts of activated carbon was added. After the mixture was stirred, a filtrate was recovered via filtration, and the filtrate was condensed to obtain 20.20 parts of a light-yellow colored oil. The obtained 20.20 parts of the light-yellow colored oil was dissolved by adding in 60.60 parts of acetonitrile, and then the mixture was condensed followed by a further adding of 81.80 parts of ethyl acetate. The obtained solution was condensed, and then 76.60 parts of methyl-tert-butyl ether was added. After the mixture was stirred, among the resulting two separated layers, the supernatant liquid was removed in order to collect the lower layer. The lower layer was condensed, and 66.00 parts of ethyl acetate was added to the obtained condensed solution. After the mixture was stirred, among the resulting two separated layers, the supernatant liquid was removed in order to collect the lower layer. The lower layer was condensed to obtain 11.96 parts of the salt (A1-1-1) (100% purity, 81.9% yield) as a light-yellow colored oil.

[Chemical Formula 41]

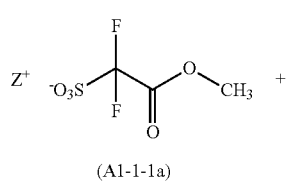

(A1-1-1a)

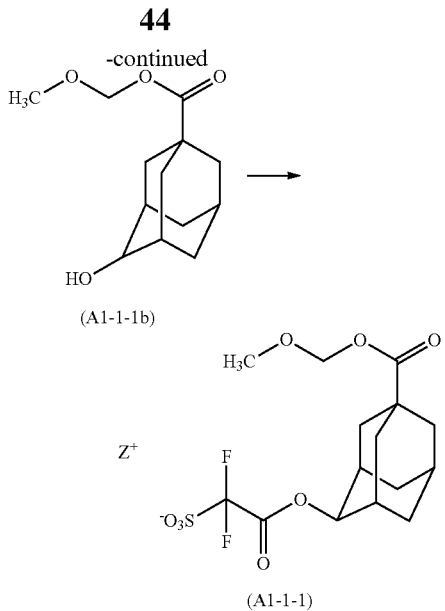

$Z^+$ : triphenyl sulfonium cation

Analytical data of the salt (A1-1-1)

MS (ESI (+) Spectrum): M+263.1

MS (ESI (−) Spectrum): M−397.1

$^1$H-NMR (dimethylsulfoxide-d$_6$, internal standard material: tetramethylsilane): δ(ppm), 1.40-2.18 (m, 13H), 3.33 (s, 3H), 4.93 (brs, 1H), 5.18 (s, 2H), 7.77-7.88 (m, 15H)

(2) Synthesis of Salt (A1-2-1)

Except for using 6.54 parts of a compound (A1-2-1b) (95.0% purity) instead of the 7.97 parts of the compound (A1-1-1b) (97.1% purity), 8.36 parts of the salt (A1-2-1) (100% purity, 62.4% yield) was obtained as a light-yellow colored oil in a manner similar to the synthesis of the salt (A1-1-1).

[Chemical Formula 42]

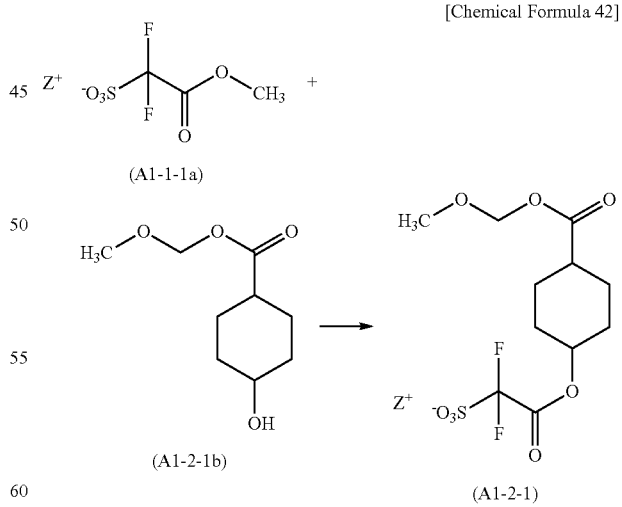

$Z^+$ : triphenyl sulfonium cation

Analytical data of the salt (A1-2-1)

MS (ESI (+) Spectrum): M+263.1

MS (ESI (−) Spectrum): M−345.1

$^1$H-NMR (dimethylsulfoxide-d$_6$, internal standard material: tetramethylsilane): δ(ppm), 1.39-1.98 (m, 8H), 2.32 (m, 1H), 3.24 (s, 3H), 3.94 (m, 1H), 5.1.8 (s, 2H), 7.77-7.88 (m, 15H)

(3) Synthesis of a Salt (A1-3-1)

Except for using 7.99 parts of a compound (A1-3-1b) (100% purity) instead of the 7.97 parts of the compound (A1-1-1b) (97.1% purity), 11.52 parts of the salt (A1-3-1) (100% purity, 79.0% yield) was obtained as a light-yellow colored oil in a manner similar to the synthesis of the salt (A1-1-1).

[Chemical Formula 43]

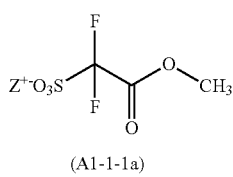

(A1-1-1a)

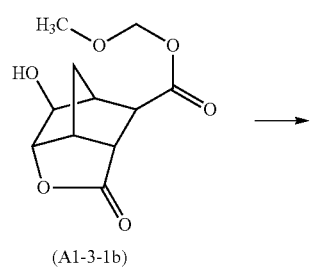

(A1-3-1b)

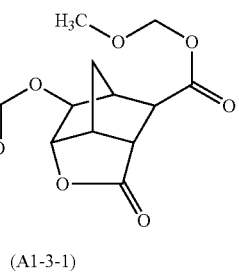

(A1-3-1)

Z$^+$: triphenyl sulfonium cation

Analytical data of the salt (A1-3-1)

MS (ESI (+) SPECTRUM): M+263.1

MS (ESI (−) SPECTRUM): M−399.0

$^1$H-NMR (dimethylsulfoxide-d$_6$, internal standard material: tetramethylsilane): δ(PPM), 1.41-2.09 (M, 3H), 2.66 (M, 1H), 2.91 (D, 1H), 2.98 (M, 1H), 3.25 (S, 3H), 4.59 (S, 1H), 4.89 (M, 1H), 5.18 (S, 2H), 7.76-7.91 (M, 15H)

(4) Synthesis of a Salt (A1-4-1)

Except for using 8.84 parts of a compound (A1-4-1b) (68.0% purity) instead of the 7.97 parts of the compound (A1-1-1b) (97.1% purity), 4.14 parts of the salt (A1-4-1) (100% purity, 31.2% yield) was obtained as a light-yellow colored oil in a manner similar to the synthesis of the salt (A1-1-1).

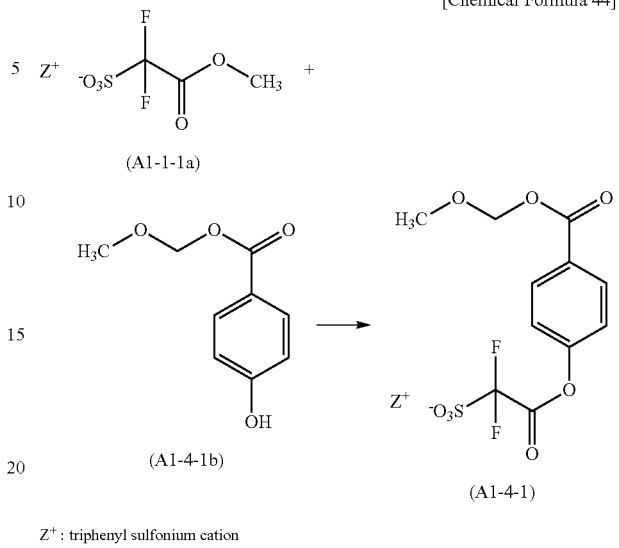

Z$^+$: triphenyl sulfonium cation

Analytical data of the salt (A1-4-1)

MS (ESI (+) Spectrum): M+263.1

MS (ESI (−) Spectrum): M−339.0

$^1$H-NMR (dimethylsulfoxide-d$_6$, internal standard material: tetramethylsilane): δ(ppm), 3.24 (s, 3H), 5.33 (s, 2H), 6.78 (m, 2H), 6.92 (m, 2H), 7.70-7.90 (m, 15H)

(5) Synthesis of a Salt (A1-1-2)

In a reaction container, a mixture comprising 6.60 parts of the salt (A1-1-1), 40.00 parts of chloroform, 7.70 parts of aqueous of 1N (1 mol/L) hydrochloric acid and 7.70 parts of methanol was prepared, and the mixture was stirred for 15 hours at 23° C. To this solution, 40.00 parts of aqueous of 1N (1 mol/L) sodium hydrogen carbonate was added, and the resultant mixture was stirred, and then the organic layer was separated and recovered. Next, 40.00 parts of ion exchanged water was added to the organic layer. After the mixture was stirred, the organic layer was separated and recovered. A water-rinsing manipulation was conducted three times on the recovered organic layer. To the water-rinsed organic layer, 1.00 parts of activated carbon was added. After the mixture was stirred, a filtrate was recovered via filtration, and the filtrate was condensed to obtain 7.71 parts of a salt (A1-1-2a) as a light-yellow colored oil.

[Chemical Formula 45]

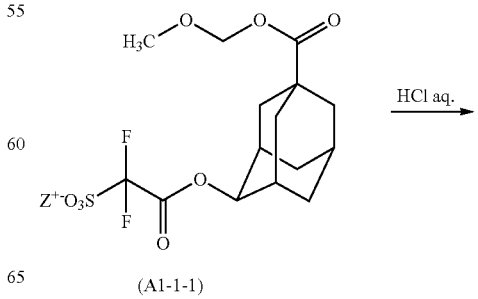

(A1-1-1)

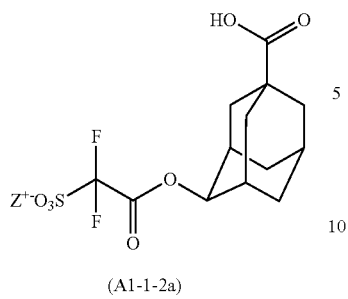

(A1-1-2a)

$Z^+$: triphenyl sulfonium cation

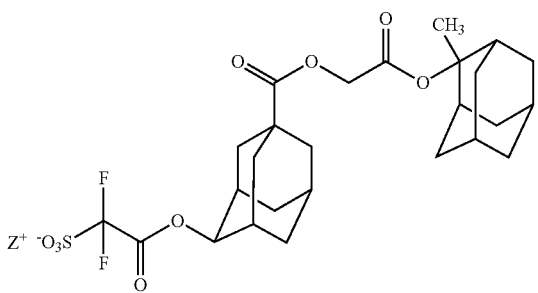

(A1-1-2)

$Z^+$: triphenyl sulfonium cation

Into a reaction container, 3.09 parts of a salt (A1-1-2a) and 15.50 parts of N,N-dimethylformamide was added and stirred at 23° C. for 30 minutes, then 0.58 parts of potassium carbonate and 0.17 parts of potassium iodide were added to the solution, and the solution was stirred at 50° C. for 1 hour. The resulting solution was cooled to 40° C., a solution in which 1.21 parts of a salt (A1-1-2b) was dissolved in 9.0 parts of N,N-dimethylformamide was dripped into the mixture, and a reaction was conducted at 40° C. for 23 hours. After that, the resulting mixture was cooled, and then 30.00 parts of chloroform and 30.00 parts of ion exchanged water were added. After the mixture was stirred, the organic layer was separated and recovered. The organic layer was repeatedly rinsed with ion exchanged water until the aqueous layer becomes neutral. To the rinsed organic layer, 1.2 parts of activated carbon was added. After the mixture was stirred, a filtrate was recovered via filtration, and the filtrate was condensed. The condensed filtrate was dissolved by adding in 10 parts of ethyl acetate, the supernatant liquid was removed to obtain a residue. To the residue, 10 parts of methyl-tert-butyl ether was added. After the mixture was stirred, among the resulting two separated layers, the supernatant liquid was removed in order to collect the residue. The residue was dissolved in chloroform and condensed to obtain 1.09 parts of the salt (A1-1-2) (100% purity, 27% yield) as an orange colored oil.

Analytical data of the salt (A1-1-2)

MS (ESI (+) Spectrum): M+263.1

MS (ESI (−) Spectrum): M−559.2

$^1$H-NMR (dimethylsulfoxide-$d_6$, internal standard material: tetramethylsilane): δ(ppm), 1.26-2.38 (m, 27H), 1.59 (s, 3H), 4.79 (s, 2H), 0.93 (brs, 1H), 7.77-7.88 (m, 15H)

(6) Synthesis of a Salt (A1-1-3)

In a reaction container, 5.88 parts of a salt (A1-1-3a) and 2.43 parts of salt (A1-1-2b) were added to 40.00 parts of dichloroethane, and stirred until the salt was dissolved. To this solution, 0.24 parts of sodium hydride was added and stirred at 23° C. for 30 minutes. After further stirring for 15 hours, 40.00 parts of ion exchanged water was added to the solution, and the organic layer was separated and recovered. A water-rinsing manipulation was conducted three times on the recovered organic layer. To the water-rinsed organic layer, 1.00 part of activated carbon was added. After the mixture was stirred, a filtrate was recovered via filtration, and the filtrate was condensed to obtain 7.90 parts of a light-yellow colored oil. The obtained 7.90 parts of the light-yellow colored oil was dissolved by adding in 24.00 parts of acetonitrile, and then the mixture was condensed followed by a further adding of 40.00 parts of ethyl acetate. The obtained solution was condensed, and then 40.00 parts of methyl-tert-butyl ether was added. After the mixture was stirred, among the resulting two separated layers, the supernatant liquid was removed in order to collect the lower layer. The lower layer was condensed, and 40.00 parts of ethyl acetate was added. After the mixture was stirred, among the resulting two separated layers, the supernatant liquid was removed in order to collect the lower layer. The lower layer was condensed to obtain 4.38 parts of the salt (A1-1-3) (100% purity, 55.1% yield) as a light-yellow colored, oil.

[Chemical Formula 46]

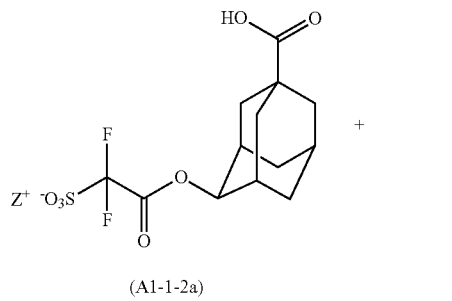

(A1-1-2a)

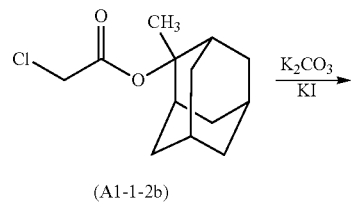

(A1-1-2b)

$\xrightarrow{K_2CO_3}{KI}$

[Chemical Formula 47]

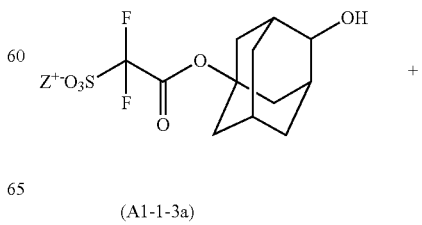

(A1-1-3a)

+

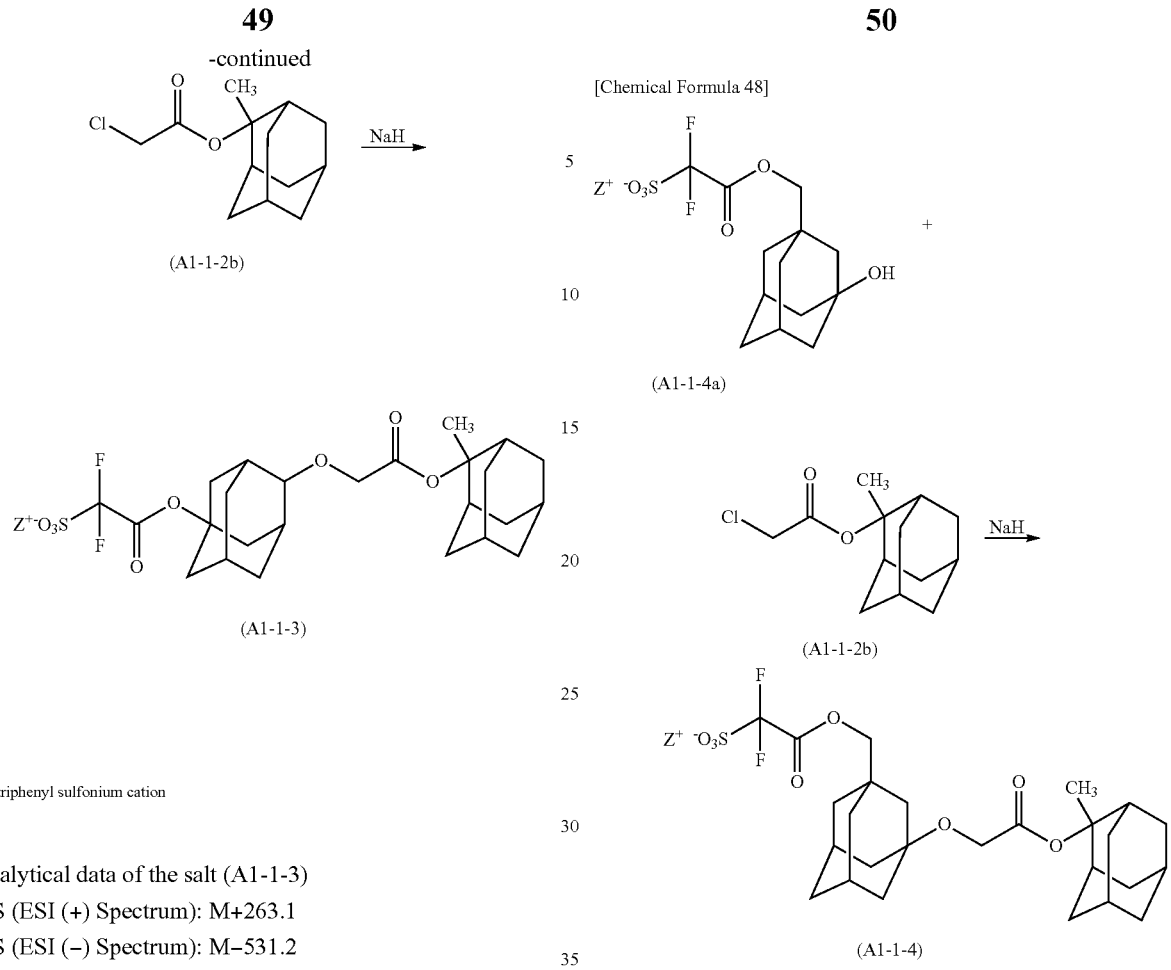

Analytical data of the salt (A1-1-3)

MS (ESI (+) Spectrum): M+263.1

MS (ESI (−) Spectrum): M−531.2

$^1$H-NMR (dimethylsulfoxide-$d_6$, internal standard material: tetramethylsilane): δ(ppm), 1.28-2.38 (m, 27H), 1.59 (s, 3H), 3.52 (m, 1H), 4.08 (s, 2H), 7.77-7.88 (m, 15H)

(7) Synthesis of a Salt (A1-1-4)

In a reaction container, 6.03 parts of a salt (A1-1-4a) and 2.43 parts of the compound (A1-1-2b) were added to 40.00 parts of dichloroethane, and stirred until the salt was dissolved. To this solution, 0.24 parts of sodium hydride was added and stirred at 23° C. for 30 minutes. After further stirring for 15 hours, 40.00 parts of ion exchanged water was added to the mixture, and the organic layer was separated and recovered. A water-rinsing manipulation was conducted three times on the recovered organic layer. To the water-rinsed organic layer, 1.00 part of activated carbon was added. After the mixture was stirred, a filtrate was recovered via filtration, and the filtrate was condensed to obtain 7.71 parts of a light-yellow colored oil. The obtained 7.71 parts of the light-yellow colored oil was dissolved by adding in 24.00 parts of acetonitrile, and then the mixture was condensed followed by a further adding of 40.00 parts of ethyl acetate. The obtained solution was condensed, and then 40.00 parts of methyl-tert-butyl ether was added. After the mixture was stirred, among the resulting two separated layers, the supernatant liquid was removed in order to collect the lower layer. The lower layer was condensed, and 40.00 parts of ethyl acetate was added. After the mixture was stirred, among the resulting two separated layers, the supernatant liquid was removed in order to collect the lower layer. The lower layer was condensed to obtain 3.28 parts of a salt (A1-1-4) (100% purity, 40.5 yield) as a light-yellow colored oil.

Analytical data of the salt (A1-1-4)

MS (ESI (+) Spectrum): M+263.1

MS (ESI (−) Spectrum): M−545.2

$^1$H-NMR (dimethylsulfoxide-$d_6$, internal standard material: tetramethylsilane): δ(ppm), 1.28-2.38 (m, 28H), 1.59 (s, 3H), 3.85 (s, 2H), 4.10 (s, 2H), 7.77-7.88 (m, 15H)

(8) Synthesis of a Salt (A2-1-1)

A salt represented by a formula (A2-1-1b) was synthesized by the method described in Japanese Laid-Open Patent Publication No. 2008-13551 (cf. paragraph [0116]). In a reaction container, 11.80 parts of a salt represented by the formula (A2-1-1b), 400 parts of chloroform and 200 parts of ion exchanged water were mixed, further, to the mixture, 20.50 parts of a salt represented by a formula (A2-1-1a) and 200 parts of ion exchanged water were added. After the mixture was stirred at 23° C. for 15 hours, the organic layer was separated and recovered. To the recovered organic layer, 200 parts of ion exchanged water was added. After the mixture was stirred at 23° C. for 30 minutes, the organic layer was separated and recovered. The water-rinsing manipulation was conducted three times on the recovered organic layer. Subsequently, the obtained organic layer was condensed, and then 200 parts of methyl-tert-butyl ether was added. After the mixture was stirred at 23° C. for 30 minutes, a filtrate was recovered via filtration to obtain 12.52 parts of a salt (A2-1-1c).

[Chemical Formula 49]

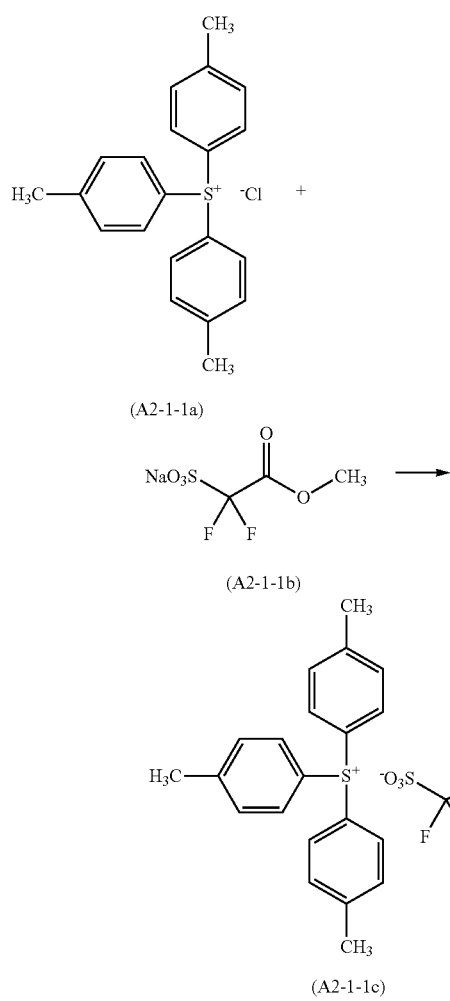

In a reaction container, 10.93 parts of the salt (A2-1-1c) was added to 80.00 parts of chloroform, and stirred until the salt was dissolved. To this solution, 7.97 parts of a compound (A1-1-1c) (97.1% purity) was added, followed by adding 0.15 parts of lithium amide (LiNH$_2$), and stirred at 23° C. for 30 minutes. Then, 13.00 parts of molecular sieve (Molecular Sieves 5A; manufactured by Wako Pure Chemical Industries, Ltd.) was added, and the mixture was stirred at 60° C. for 8 hours. The resulting mixture was then cooled to 23° C., and filtered to obtain a filtrate. The filtrate was mixed with 25.00 parts of ion exchanged water and then stirred. After the mixture was stirred, the organic layer was separated and recovered. A water-rinsing manipulation was conducted twice on the recovered organic layer. To the water-rinsed organic layer, 1.20 parts of activated carbon was added. After the mixture was stirred, a filtrate was recovered via filtration, and the filtrate was condensed to obtain 21.23 parts of a light-yellow colored oil. The obtained 21.23 parts of the light-yellow colored oil was dissolved by adding in 63.69 parts of acetonitrile, and then the mixture was condensed followed by a further adding of 84.92 parts of ethyl acetate. The obtained solution was condensed, and then 80.00 parts of methyl-tert-butyl ether was added. After the mixture was stirred, among the resulting two separated layers, the supernatant liquid was removed in order to collect the lower layer. The lower layer was condensed, and 70.00 parts of ethyl acetate was added to the obtained condensed solution. After the mixture was stirred, among the resulting two separated layers, the supernatant liquid was removed in order to collect the lower layer. The lower layer was condensed to obtain 12.04 parts of the salt (A2-1-1).

[Chemical Formula 50]

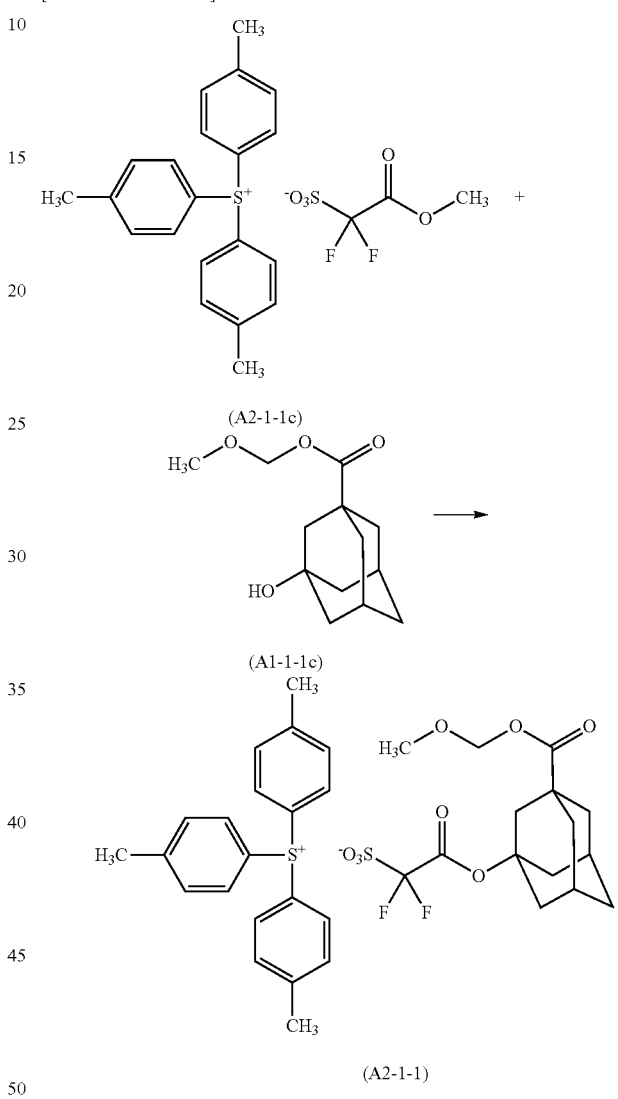

Analytical data of the salt (A2-1-1)
MS (ESI (+) Spectrum): M+305.1
MS (ESI (−) Spectrum): M−397.1

(9) Synthesis of a Salt (A3-1-1)

In a reaction container, 11.80 parts of a salt (A2-1-1b), 400 parts of chloroform and 200 parts of ion exchanged water was mixed, further, to the mixture, 18.00 parts of a salt represented by a formula (A3-1-1a) and 200 parts of ion exchanged water were added. After the mixture was stirred at 23° C. for 30 minutes, the organic layer was separated and recovered. This water-rinsing manipulation was conducted three times on the recovered organic layer. Subsequently, the obtained organic layer was condensed, and then 150 parts of methyl-tert-butyl ether was added. After the mixture was stirred at 23° C. for 30 minutes, a filtrate was recovered via filtration to obtain 11.81 parts of a salt (A3-1-1c).

[Chemical Formula 51]

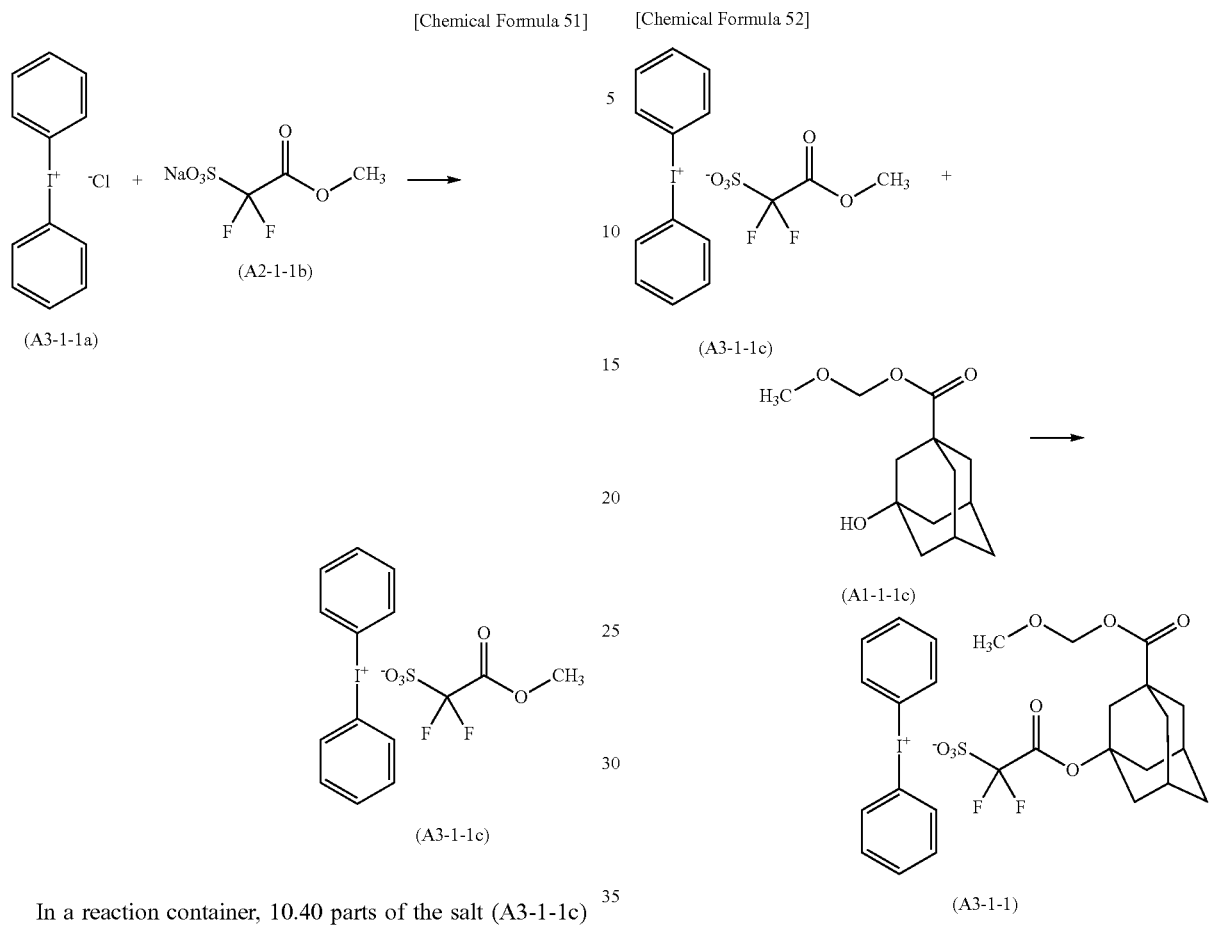

In a reaction container, 10.40 parts of the salt (A3-1-1c) was added to 80.00 parts of chloroform, and stirred until the salt was dissolved. To this solution, 7.97 parts of a compound (A1-1-1c) (97.1% purity) was added, followed by adding 0.15 parts of lithium amide (LiNH$_2$), and stirred at 23° C. for 30 minutes. Then, 13.00 parts of molecular sieve (Molecular Sieves 5A; manufactured by Wako Pure Chemical Industries, Ltd.) was added, and the mixture was stirred at 60° C. for 8 hours. The resulting mixture was then cooled to 23° C., and filtered to obtain a filtrate. The filtrate was mixed with 24.53 parts of ion exchanged water and then stirred. After the mixture was stirred, the organic layer was separated and recovered. A water-rinsing manipulation was conducted twice on the recovered organic layer. To the water-rinsed organic layer, 1.00 parts of activated carbon was added. After the mixture was stirred, a filtrate was recovered via filtration, and the filtrate was condensed to obtain 20.18 parts of a light-yellow colored oil. The obtained 20.18 parts of the light-yellow colored oil was dissolved by adding in 60.54 parts of acetonitrile, and then the mixture was condensed followed by a further adding of 81.72 parts of ethyl acetate. The obtained solution was condensed, and then 80.00 parts of methyl-tert-butyl ether was added. After the mixture was stirred, among the resulting two separated layers, the supernatant liquid was removed in order to collect the lower layer. The lower layer was condensed, and 60.00 parts of ethyl acetate was added to the obtained condensed solution. After the mixture was stirred, among the resulting two separated layers, the supernatant liquid was removed in order to collect the lower layer. The lower layer was condensed to obtain 11.57 parts of the salt (A3-1-1).

Analytical data of the salt (A3-1-1)
MS (ESI (+) Spectrum): M+281.0
MS (ESI (−) Spectrum): M−397.1

(10) Synthesis of a Salt (A4-1-1)

In a reaction container, 11.80 parts of a salt (A2-1-1b), 300 parts of chloroform and 150 parts of ion exchanged water were mixed, further, to the mixture, 16.33 parts of a salt represented by a formula (A4-1-1a) and 150 parts of ion exchanged water were added. After the mixture was stirred at 23° C. for 15 hours, the organic layer was separated and recovered. To the recovered organic layer, 150 parts of ion exchanged water was added. After the mixture was stirred at 23° C. for 30 minutes, the organic layer was separated and recovered. The water-rinsing manipulation was conducted three times on the recovered organic layer. Subsequently, the obtained organic layer was condensed, and then 150 parts of methyl-tert-butyl ether was added. After the mixture was stirred at 23° C. for 30 minutes, a filtrate was recovered via filtration to obtain 10.21 parts of a salt (A4-1-1c).

[Chemical Formula 53]

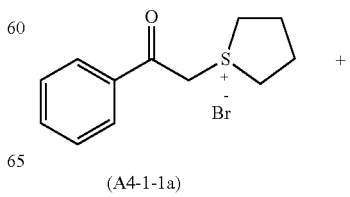

(A4-1-1a)

-continued (A2-1-1b)

(A4-1-1c)

In a reaction container, 8.77 parts of the salt (A4-1-1c) was added to 70.00 parts of chloroform, and stirred until the salt was dissolved. To this solution, 7.97 parts of a compound (A1-1-1c) (97.1% purity) was added, followed by adding 0.15 parts of lithium amide (LiNH$_2$), and stirred at 23° C. for 30 minutes. Then, 10.00 parts of molecular sieve (Molecular Sieves 5A; manufactured by Wako Pure Chemical Industries, Ltd.) was added, and the mixture was stirred at 60° C. for 8 hours. The resulting mixture was then cooled to 23° C., and filtered to obtain a filtrate. The filtrate was mixed with 20.00 parts of ion exchanged water and then stirred. After the mixture was stirred, the organic layer was separated and recovered. A water-rinsing manipulation was conducted twice on the recovered organic layer. To the water-rinsed organic layer, 1.00 parts of activated carbon was added. After the mixture was stirred, a filtrate was recovered via filtration, and the filtrate was condensed to obtain 15.73 parts of a light-yellow colored oil. The obtained 15.73 parts of the light-yellow colored oil was dissolved by adding in 47.19 parts of acetonitrile, and then the mixture was condensed followed by a further adding of 62.92 parts of ethyl acetate. The obtained solution was condensed, and then 60.00 parts of methyl-tert-butyl ether was added. After the mixture was stirred, among the resulting two separated layers, the supernatant liquid was removed in order to collect the lower layer. The lower layer was condensed, and 40.00 parts of ethyl acetate was added to the obtained condensed solution. After the mixture was stirred, among the resulting two separated layers, the supernatant liquid was removed in order to collect the lower layer. The lower layer was condensed to obtain 8.28 parts of the salt (A4-1-1).

[Chemical Formula 54]

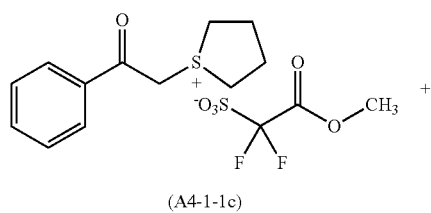

(A4-1-1c)

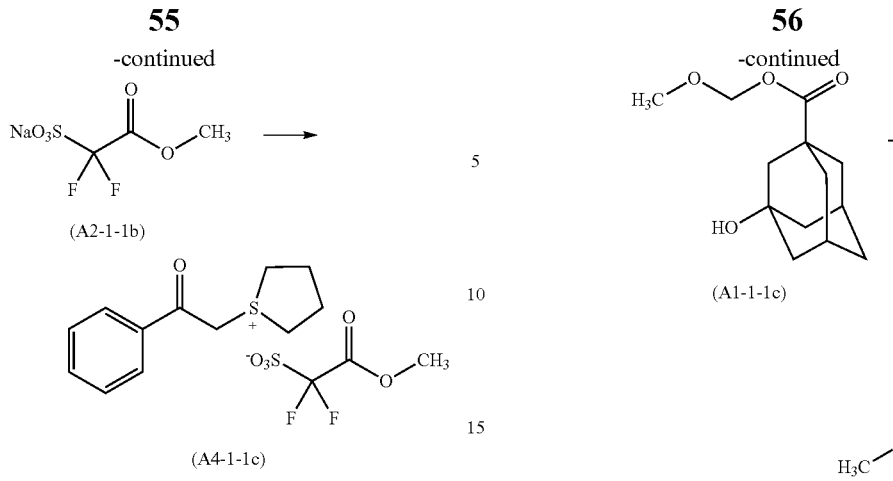

(A1-1-1c)

(A4-1-1)

Analytical data of the salt (A4-1-1)

MS (ESI (+) Spectrum): M+207.1

MS (ESI (−) Spectrum): M−397.1

(11) Synthesis of a Salt (A5-1-2)

In a reaction container, 10.4 parts of Lithium aluminum hydride and 120 parts of anhydrous tetrahydrofuran were mixed and stirred at 23° C. for 30 minutes. Next, while cooling in an ice bath, a solution in which 62.2 parts of a compound represented by a formula (A5-1-2a) was dissolved in 900 parts of anhydrous tetrahydrofuran was dripped into the mixture, and stirred at 23° C. for five hours. To the reactant mass, 50.0 parts of ethyl acetate and 50.00 parts of 6N (6 mol/L) hydrochloric acid were added. After the mixture was stirred, the organic layer was separated and recovered. The recovered organic layer was condensed, and the condensed organic layer was purified by silica gel column chromatography (silica gel 60-200 mesh, available from Merck Ltd., eluent: chloroform/methanol=5/1), consequently 84.7 parts of a compound represented by a formula (A5-1-2b) (60% purity) was obtained.

At the room temperature, 4.55 parts of a compound represented by a formula (A5-1-2c) was mixed with 90 parts of anhydrous tetrahydrofuran, and the mixture was stirred at the room temperature for 30 minute to dissolve the compound. Into the obtained solution, a mixed solution of 3.77 parts of carbonyldiimidazole and 45 parts of anhydrous tetrahydrofuran was dripped at the room temperature, and the mixture was stirred at 23° C. for 4 hours. The obtained reaction solution was dripped into a mixed solution of 7.87 parts of a salt (A5-1-2b) (60% purity) and 50 parts of anhydrous tetrahydrofuran for 30 minutes at 55° C. The reaction solution was heated at 65° C. for 18 hours, after the reaction solution was cooled and filtrated to obtain a filtrate, and the filtrate was condensed. The condensed filtrate was purified by silica gel column chromatography (silica gel 60-200 mesh, available from Merck Ltd., eluent: chloroform/methanol=5/1) to obtain 4.44 parts of a compound represented by a formula (A5-1-2d).

[Chemical Formula 55]

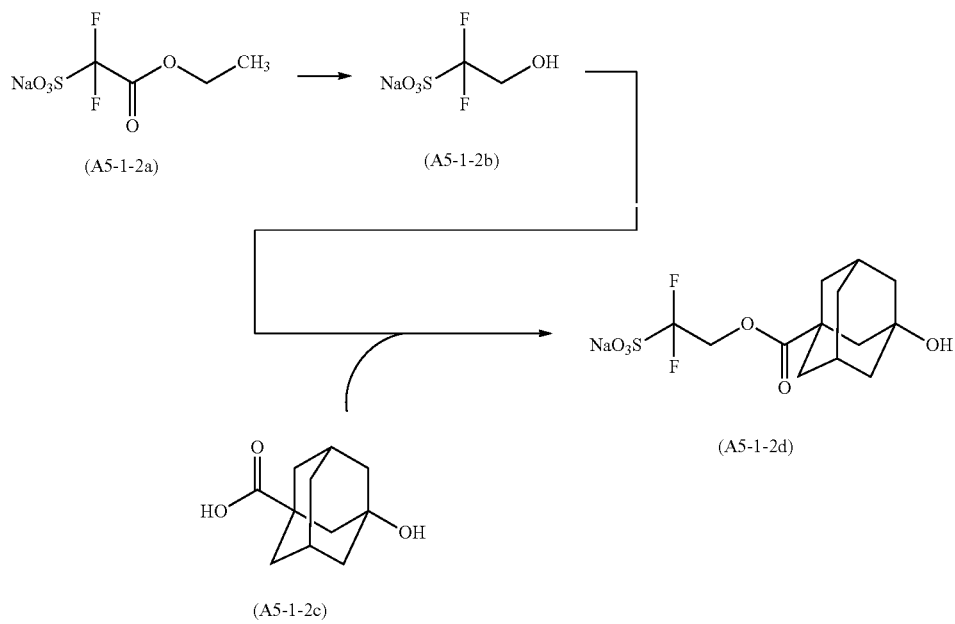

Next, 1.01 parts of the compound represented by the formula (A5-1-2d) and 20 parts of chloroform were mixed and stirred at 23° C. for 30 minutes, further, 6.3 parts of a compound represented by a formula (A5-1-2e) (13.1% aqueous solution) was added to this mixture at 23° C. After the mixture was stirred at the room temperature for 12 hours, the organic layer was separated and recovered. The recovered organic layer was water-rinsed by adding 10.0 parts of ion exchanged water. The organic layer was separated and recovered, and this water-rinsing manipulation was repeated five times. To the rinsed organic layer, 1.00 parts of magnesium sulfate was added. After the mixture was stirred at 23° C. for 30 minutes, a filtrate was recovered via filtration, and the filtrate was condensed to obtain 1.28 parts of a compound represented by a formula (A5-1-2g).

[Chemical Formula 56]

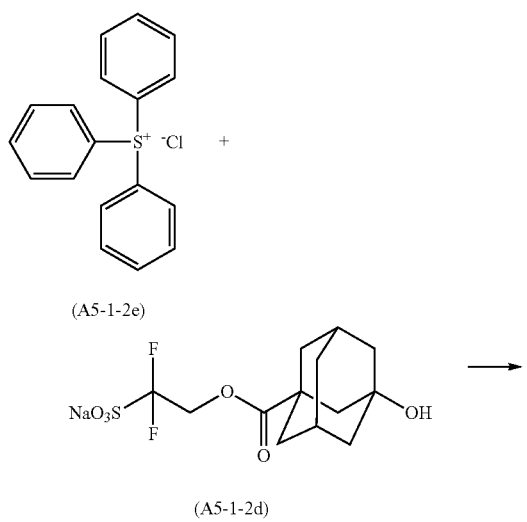

-continued

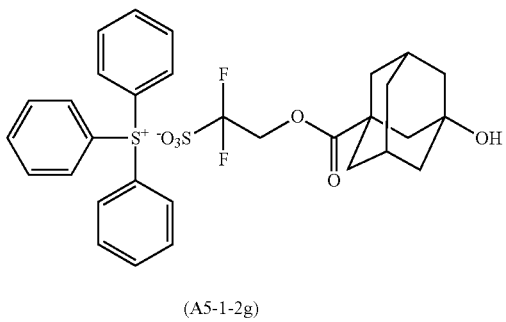

In a reaction container, 6.03 parts of the salt (A5-1-2g) and 2.43 parts of the compound (A1-1-2b) were added to 40.00 parts of dichloroethane, and stirred until the salt and the compound were dissolved. To this solution, 0.24 parts of sodium hydride was added and stirred at 23° C. for 30 minutes. After further stirring for 15 hours, 40.00 parts of ion exchanged water was added to the solution, and the organic layer was separated and recovered. A water-rinsing manipulation was conducted three times on the recovered organic layer. To the water-rinsed organic layer, 1.00 part of activated carbon was added. After the mixture was stirred, a filtrate was recovered via filtration, and the filtrate was condensed to obtain 6.98 parts of a light-yellow colored oil. The obtained 6.98 parts of the light-yellow colored oil was dissolved by adding in 21.00 parts of acetonitrile, and then the mixture was condensed followed by a further adding of 30.00 parts of ethyl acetate. The obtained solution was condensed, and then 30.00 parts of methyl-tert-butyl ether was added. After the mixture was stirred, among the resulting two separated layers, the supernatant liquid was removed in order to collect the lower layer. The lower layer was condensed, and 30.00 parts of ethyl acetate was added. After the mixture was stirred, among the resulting two-separated layers, the supernatant liquid was removed in order to collect the lower layer. The lower layer was condensed to obtain 2.84 parts of the salt (A5-1-2).

[Chemical Formula 57]

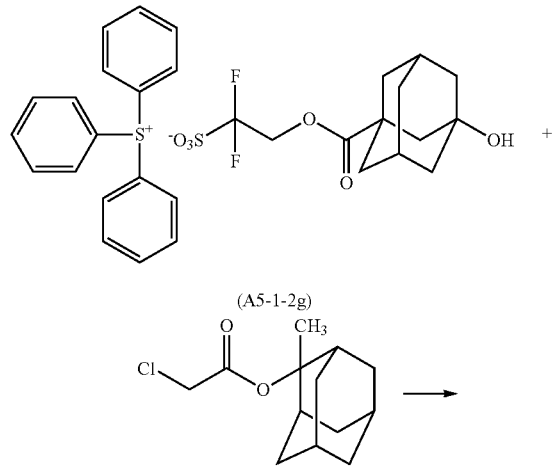

(A5-1-2g)

(A1-1-2b)

(A5-1-2)

Analytical data of the salt (A5-1-2)
MS (ESI (+) Spectrum): M+263.1
MS (ESI (−) Spectrum): M−545.2

(12) Synthesis of a Salt (A6-1-1)

The salt represented by the formula (A2-1-1b) was synthesized by the method described in Japanese Laid-Open Patent Publication No. 2008-13551. In a reaction container, 11.80 parts of the salt represented by the formula (A2-1-1b), 400 parts of chloroform and 200 parts of ion exchanged water were mixed, followed by adding 21.34 part of a salt (A6-1-1a) and 200 parts of ion exchanged water. After the mixture was stirred at 23° C. for 15 hours, the organic layer was separated and recovered. To the recovered organic layer, 200 parts of ion exchanged water was added. After the mixture was stirred at 23° C. for 30 minutes, the organic layer was separated and recovered. The water-rinsing manipulation was conducted three times on the recovered organic layer. Subsequently, the obtained organic layer was condensed, and then 200 parts of methyl-tert-butyl ether was added. After the mixture was stirred at 23° C. for 30 minutes, a filtrate was recovered via filtration to obtain 13.04 parts of a salt represented by a formula (A6-1-1c).

[Chemical Formula 58]

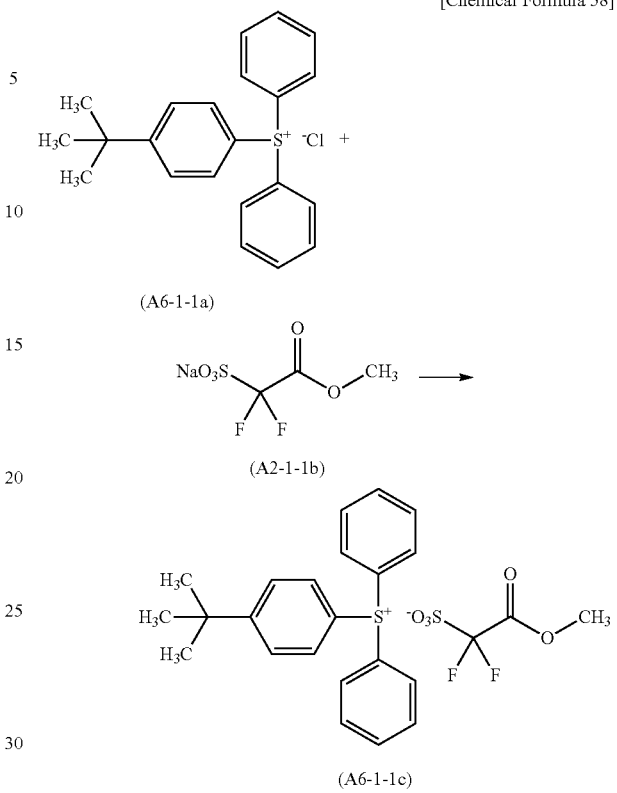

(A6-1-1a)

(A2-1-1b)

(A6-1-1c)

In a reaction container, 11.24 parts of the salt (A6-1-1c) was added to 80.00 parts of chloroform, and stirred until the salt was dissolved. To this solution, 7.97 parts of a compound (A1-1-1c) (97.1% purity) was added, followed by adding 0.15 parts of lithium amide ($LiNH_2$), and stirred at 23° C. for 30 minutes. Then, 13.00 parts of molecular sieve (Molecular Sieves 5A; manufactured by Wako Pure Chemical Industries, Ltd.) was added, and the mixture was stirred at 60° C. for 8 hours. The resulting mixture was then cooled to 23° C., and filtered to obtain a filtrate. The filtrate was mixed with 25.00 parts of ion exchanged water and then stirred. After the mixture was stirred, the organic layer was separated and recovered. A water-rinsing manipulation was conducted twice on the recovered organic layer. To the water-rinsed organic layer, 1.00 parts of activated carbon was added. After the mixture was stirred, a filtrate was recovered via filtration, and the filtrate was condensed to obtain 22.68 parts of a light-yellow colored oil. The obtained 22.68 parts of the light-yellow colored oil was dissolved by adding in 68.04 parts of acetonitrile, and then the mixture was condensed followed by a further adding of 90.72 parts of ethyl acetate. The obtained solution was condensed, and then 90.00 parts of methyl-tert-butyl ether was added. After the mixture was stirred, among the resulting two separated layers, the supernatant liquid was removed in order to collect the lower layer. The lower layer was condensed, and 80.00 parts of ethyl acetate was added to the obtained condensed solution. After the mixture was stirred, among the resulting two separated layers, the supernatant liquid was removed in order to collect the lower layer. The lower layer was condensed to obtain 12.39 parts of the salt (A6-1-1).

[Chemical Formula 59]

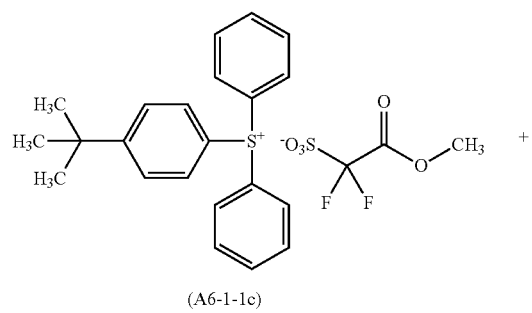

(A6-1-1c)

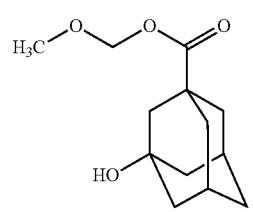

(A1-1-1c)

→

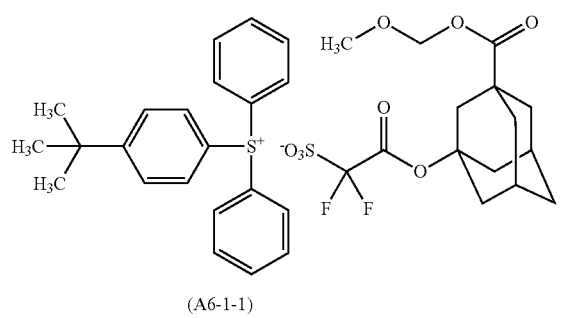

(A6-1-1)

Analytical data of the salt (A6-1-1)

MS (ESI (+) Spectrum): M+319.2

MS (ESI (−) Spectrum): M−397.1

2. Synthesis of the Resin

[Synthesis of a Resin B1]

The monomer (b1-1-1), the monomer (b2-1-1) and the monomer (b3-1-1) were blended at a molar ratio of 50:25:25. Dioxane whose weight was 1.5 times the total weight of all the monomers was added thereto to obtain a monomer mixture. Azobisisobutyronitrile and azobis(2,4-dimethylvaleronitrile), as an initiator, were added, at 1 mole % and 3 mole %, respectively, with respect to the total amount of all the monomers, to the mixture, and were heated at 77° C. for about five hours. Thereafter, a large amount of mixture of water and methanol (methanol: water=4:1) was poured into the reaction solution to cause precipitation and then filtrate. Purification was performed by pouring the obtained residue into a large amount of methanol, and a repulping-manipuration was performed three times. Consequently, a copolymer having an Mw of about 8,000 was obtained in a yield of 60%. The copolymer had structural units corresponding to the respective monomers, and was used as the resin (B1).

[Chemical formula 60]

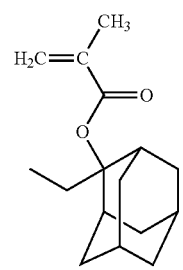

(b1-1-1)

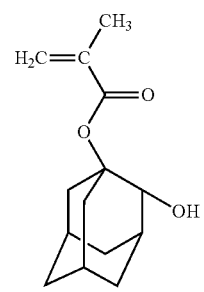

(b2-1-1)

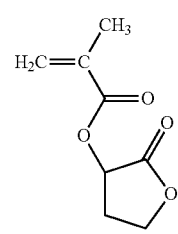

(b3-1-1)

[Synthesis of a Resin B2]

The monomers (b1-1-1), (b1-2-1), (b2-1-1), (b3-1-1) and (b3-2-1) were blended at a molar ratio of 30:14:6:20:30. Dioxane whose weight was 1.5 times the total weight of all the monomers was added thereto to obtain a monomer mixture. Azobisisobutyronitrile and azobis(2,4-dimethylvaleronitrile), as an initiator, were added, at 1 mole % and 3 mole %, respectively, with respect to the total amount of all the monomers, to the mixture, and were heated at 77° C. for about five hours. Thereafter, a large amount of mixture of water and methanol (methanol: water=4:1) was poured into the reaction solution to cause precipitation and then filtrate. Purification was performed by pouring the obtained residue into a large amount of methanol, and a repulping-manipuration was performed three times. Consequently, a copolymer having an Mw of about 7,000 was obtained in a yield of 68%. The copolymer had structural units corresponding to the respective monomers, and was used as the resin (B2).

[Chemical formula 61]

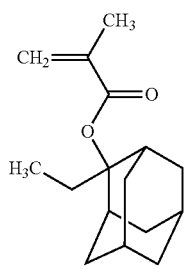

(b1-1-1)

(b1-2-1)

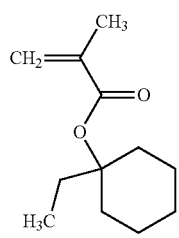

(b2-1-1)

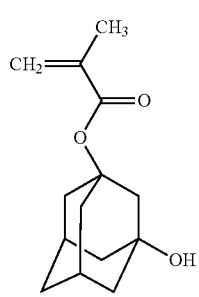

(b3-1-1)

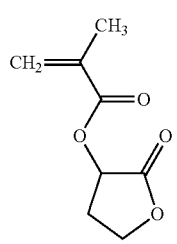

(b3-2-1)

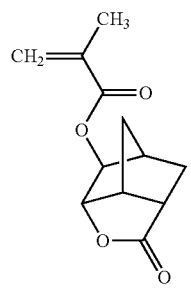

3. Preparation of the Resist Composition and Property Evaluation

The each salt (A1-1-1), (A1-1-2), (A1-1-3), (A1-1-4), (A1-2-1), (A1-3-1), (A1-4-1), (A2-1-1), (A3-1-1), (A4-1-1), (A5-1-2) or (A6-1-1) obtained by the above mentioned manner, the resin (B1) or the resin (B2), a solvent and each component indicated in Table 1 were mixed, dissolved and filtered through a fluorine resin filter having a pore diameter of 0.2 μm, to prepare a liquid resist composition. The resist pattern was formed by using the resist composition according to the following method, the properties of the resist pattern (resolution and mask error enhancement factor) were evaluated. For comparison, a resist composition (production example No. 20) was prepared by using an acid generator represented by a formula (X) (triphenylsulfonium 1-adamantylmethoxy-carbonyl difluoromethanesulfonate), and the properties thereof were also evaluated. The evaluation results were also indicated in Table 2.

TABLE 1

| Production Example | Resin (B) Kind | Amount | Acid-generator (A) Kind | Amount | Basic compound (C) Kind | Amount | $T_{PB}$ | $T_{PEB}$ |
|---|---|---|---|---|---|---|---|---|
| No. 1  | B1 | 10 parts | A1-1-1 | 0.7 parts | C1 | 0.065 parts | 100° C. | 100° C. |
| No. 2  | B1 | 10 parts | A1-1-2 | 0.7 parts | C1 | 0.065 parts | 100° C. | 100° C. |
| No. 3  | B1 | 10 parts | A1-1-3 | 0.7 parts | C1 | 0.065 parts | 100° C. | 100° C. |
| No. 4  | B1 | 10 parts | A1-1-4 | 0.7 parts | C1 | 0.065 parts | 100° C. | 100° C. |
| No. 5  | B1 | 10 parts | A1-2-1 | 0.7 parts | C1 | 0.065 parts | 100° C. | 100° C. |
| No. 6  | B1 | 10 parts | A1-3-1 | 0.7 parts | C1 | 0.065 parts | 100° C. | 100° C. |
| No. 7  | B1 | 10 parts | A1-4-1 | 0.7 parts | C1 | 0.065 parts | 100° C. | 100° C. |
| No. 8  | B2 | 10 parts | A1-1-1 | 0.7 parts | C1 | 0.065 parts | 100° C. | 100° C. |
| No. 9  | B2 | 10 parts | A1-1-2 | 0.7 parts | C1 | 0.065 parts | 100° C. | 100° C. |
| No. 10 | B2 | 10 parts | A1-1-3 | 0.7 parts | C1 | 0.065 parts | 100° C. | 100° C. |
| No. 11 | B2 | 10 parts | A1-1-4 | 0.7 parts | C1 | 0.065 parts | 100° C. | 100° C. |
| No. 12 | B2 | 10 parts | A1-2-1 | 0.7 parts | C1 | 0.065 parts | 100° C. | 100° C. |
| No. 13 | B2 | 10 parts | A1-3-1 | 0.7 parts | C1 | 0.065 parts | 100° C. | 100° C. |
| No. 14 | B2 | 10 parts | A1-4-1 | 0.7 parts | C1 | 0.065 parts | 100° C. | 100° C. |
| No. 15 | B2 | 10 parts | A2-1-1 | 0.7 parts | C1 | 0.065 parts | 100° C. | 100° C. |
| No. 16 | B2 | 10 parts | A3-1-1 | 0.7 parts | C1 | 0.065 parts | 100° C. | 100° C. |
| No. 17 | B2 | 10 parts | A4-1-1 | 0.7 parts | C1 | 0.065 parts | 100° C. | 100° C. |
| No. 18 | B2 | 10 parts | A5-1-2 | 0.7 parts | C1 | 0.065 parts | 100° C. | 100° C. |
| No. 19 | B2 | 10 parts | A6-1-1 | 0.7 parts | C1 | 0.065 parts | 100° C. | 100° C. |
| No. 20 | B1 | 10 parts | X | 0.7 parts | C1 | 0.065 parts | 100° C. | 100° C. |

In the table 1, the resins B1, B2, the acid generator X, the basic compound C1 and the solvent are as follows.
<Resin>
The resin B1 and B2: see the above described synthesis
<Acid-Generator>
The acid generator X:

[Chemical Formula 62]

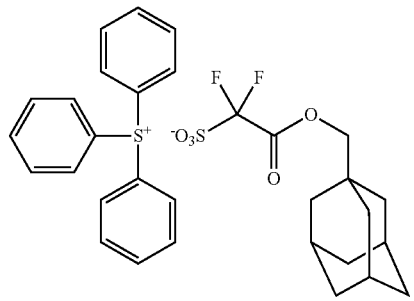

<Basic Compound>
Basic compound (C)=2,6-diisopropylaniline
<Solvent>
Propylene glycol monomethyl ether acetate: 265 parts
2-Heptanone: 20.0 parts
Propylene glycol monomethyl ether: 20.0 parts
γ-Butyrolactone: 3.5 parts (1) Preparation of a Resist Pattern Silicon wafers were each coated with an organic anti-reflective coating composition (ARC-29; manufactured by Nissan Chemical Industries, Ltd.), and were baked under the conditions of 205° C. for 60 seconds, to form an organic anti-reflective coating having a thickness of 780 Å. Subsequently, the resist composition was spin-coated over the organic anti-reflective coating such that a dried film had a thickness of 85 nm. The silicon wafers each coated with the resist composition were prebaked on a direct hot plate at a temperature ($T_{PB}$) as indicated in Table 1 for 60 seconds, to form a resist film. On a silicon wafer on which a pre-baked resist film as described above has been formed, a line-and-space pattern was exposed with gradually varied amounts of exposure, via a mask having a dark field line-and-space pattern using an ArF excimer stepper (FPA5000-AS3; manufactured by Canon Inc., NA=0.75, 2/3 Annular). Here, a term "mask having a dark field line-and-space pattern" refers to a mask having a translucent portion (glass surface) formed on a light-blocking portion (chromium layer) of a base, while the line width of the light-blocking portion to the line width of the translucent portion is 1:1, and the light-blocking portion is on the external side and the translucent portion is in the internal side.

After the exposure, each silicon wafer was subjected to post-exposure-baking on a hotplate at a temperature ($T_{PEB}$) as indicated in Table 1, for 60 seconds. Subsequently, each silicon wafer was subjected to puddle development for 60 seconds by using a 2.38 mass % aqueous tetramethylammonium hydroxide solution.

An amount of exposure, which results in a resist pattern that has a 100 nm line width which is formed with a mask for forming a line-and-space pattern having a 100 nm line width, is defined as an "effective sensitivity for line width of 100 nm"; and an amount of exposure, which results in a resist pattern having a 85 nm line width which is formed with a mask for forming a line-and-space pattern having an 85 nm line width, is defined as an "effective sensitivity for line width of 85 nm". The line widths of the resist patterns were measured by using a scanning electron microscope (S-4100; manufactured by Hitachi Ltd.).

(2) Evaluation of Resolution

Resolutions were evaluated as follows by defining production example No. 20 (comparative example) as a standard (S). Specifically, at the effective sensitivity for line width of 100 nm, it was examined if a pattern can be resolved even when a mask for forming a line width smaller than 100 nm is used. An evaluation of G (good) is given, if the pattern can be resolved even when a mask having a line width of smaller than that of production example No. 20 is used; an evaluation of S (standard) is given, if the pattern can be resolved only with a mask having a line width equivalent to that of production example No. 20; and an evaluation of P (poor) is given, if the pattern can be resolved only with a mask having a line width larger than that of production example No. 20.

(3) Evaluation of Mask Error Enhancement Factor (MEEF)

Patterns were formed using masks for sizes of 90 nm, 95 nm, and 100 nm, at effective sensitivities for line width of 85 nm. A slope of a plotted straight line, which is obtained when the size of the mask was assigned to the horizontal axis and the line width of the pattern formed using each mask was assigned to the vertical axis, was calculated, and the slope was used as MEEF. The MEEF of production example No. 20 (comparative example) was defined as a standard (S), and in comparison with this, one with a smaller MEEF is given an evaluation of G (Good), one with a similar MEEF is given an evaluation of S (standard), and one with a larger MEEF is given an evaluation of P (poor).

TABLE 2

| Production Example | Resolution | MEEF |
|---|---|---|
| No. 1 | G | G |
| No. 2 | G | G |
| No. 3 | G | G |
| No. 4 | S | G |
| No. 5 | G | G |
| No. 6 | G | G |
| No. 7 | G | G |
| No. 8 | G | G |
| No. 9 | G | G |
| No. 10 | G | G |
| No. 11 | S | G |
| No. 12 | G | G |
| No. 13 | G | G |
| No. 14 | G | G |
| No. 15 | G | G |
| No. 16 | G | G |
| No. 17 | S | G |
| No. 18 | G | G |
| No. 19 | G | G |
| No. 20 | S | S |

From the results indicated in Table 2, it is found that resist compositions (Production Example No. 1-No. 19), in which the salt (A1) of the present invention is used as an acid generator, exhibit fine Mask Error Enhancement Factors when compared to a resist composition (Production Example No. 20) in which a conventional acid generator is used. In addition, a resolution equal to or higher than that obtained in the conventional art can be achieved if the salt (A1) of the present invention is used.

The salt (A1) of the present invention is useful for an acid generator for a chemically amplified resist composition. The resist composition comprising the salt (A1) exhibits resolution which is equal to or higher than that of the conventional one, and moreover, mask error enhancement factors of the resist composition which is superior to that of the conventional one. Further, the resist composition comprising the salt (A1) is useful for an ArF or KrF excimer laser lithography and an ArF immersion exposure lithography.

This application is based on Japanese Patent application serial no. 2009-174792 filed in Japan Patent Office on Jul. 27, 2009, the contents of which are hereby incorporated by reference.

What is claimed is:
1. A salt represented by formula (A1):

[Chemical Formula 1]

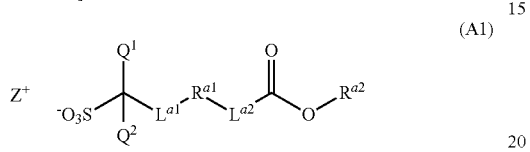

(A1)

wherein $Z^+$ represents an organic cation, $Q^1$ and $Q^2$ each independently represent a fluorine atom or a linear or branched $C_{1-6}$ perfluoroalkyl group, $L^{a1}$ represents —$(CH_2)_{m1}$—, m1 represents an integer ranging from 1 to 6, a methylene group contained in the —$(CH_2)_{m1}$— may be replaced by an oxygen atom (—O—) or a carbonyl group (—CO—), at least one hydrogen atom of the —$(CH_2)_{m1}$— may be replaced with a linear or branched $C_{1-4}$ aliphatic hydrocarbon group, $L^{a2}$ represents a single bond, —O— $(CH_2)_{L1}$—, or —CO—O—$(CH_2)_{L1}$—, L1 represents an integer ranging from 1 to 6, a methylene group contained in the —$(CH_2)_{L1}$— may be replaced with an oxygen atom or a carbonyl group, at least one hydrogen atom of the —$(CH_2)_{L1}$— may be replaced with a linear or branched $C_{1-4}$ aliphatic hydrocarbon group, $R^{a1}$ represents a $C_{4-36}$ divalent alicyclic hydrocarbon group or a $C_{6-18}$ divalent aromatic hydrocarbon group, and at least one hydrogen atom of the alicyclic hydrocarbon group or the aromatic hydrocarbon group may be replaced with a halogen atom, a linear, branched or cyclic $C_{1-12}$ aliphatic hydrocarbon group, a $C_{7-21}$ aralkyl group, a glycidyloxy group, or a $C_{2-4}$ acyl group, at least one hydrogen atom of the alicyclic hydrocarbon group may be replaced with a $C_{6-20}$ aromatic hydrocarbon group, a methylene group contained in the linear, branched or cyclic aliphatic hydrocarbon group, or the aralkyl group may be replaced with an oxygen atom or a carbonyl group, $R^{a2}$ represents an elimination group represented by the formula (II-1) or (II-2);

[Chemical Formula 2]

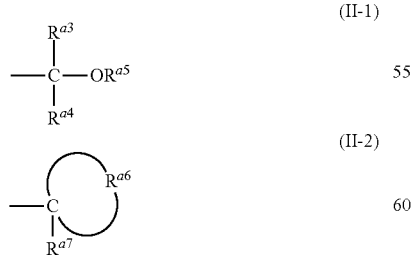

(II-1)

(II-2)

wherein $R^{a3}$ and $R^{a4}$ each independently represent a hydrogen atom or a linear or branched $C_{1-12}$ aliphatic hydrocarbon group, $R^{a5}$ represents a linear, branched or cyclic $C_{1-24}$ aliphatic hydrocarbon group, $R^{a6}$ represents a $C_{2-24}$ divalent aliphatic hydrocarbon group, and $R^{a7}$ represents a linear or branched $C_{1-12}$ aliphatic hydrocarbon group.

2. The salt according to claim 1, wherein $R^{a1}$ is represented by any of formulae (I-1), (I-2), (I-3), and (I-4):

[Chemical Formula 3]

(I-1)

(I-2)

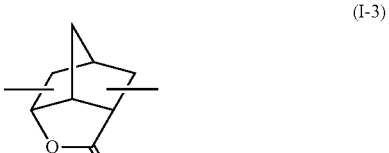

(I-3)

(I-4)

3. The salt according to claim 1, wherein $L^{a1}$ is —CO—O— or —CO—O—$(CH_2)_{k1}$—, and K1 is an integer of 1 to 4.

4. The salt according to claim 1, wherein an anion constituting the salt is represented by any of formulae (a1-1-1), (a1-1-2), (a1-1-3), (a1-1-4), (a1-1-5), (a1-2-1), (a1-3-1), (a1-4-1), and (a1-5-1):

[Chemical Formula 4]

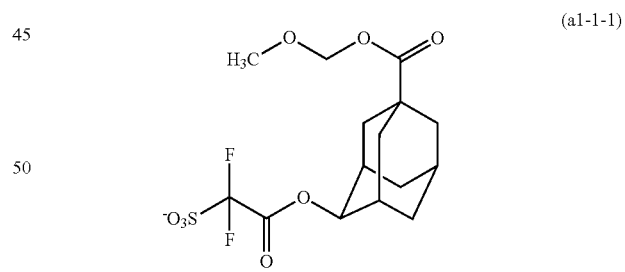

(a1-1-1)

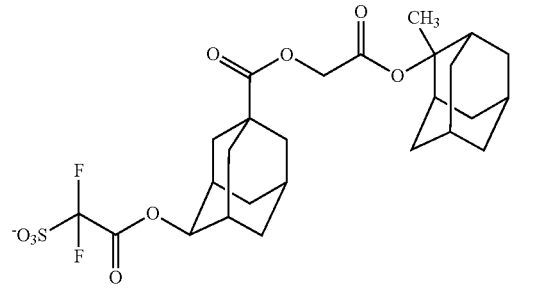

(a1-1-2)

(a1-1-3)
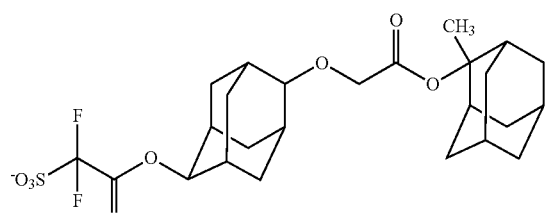

(a1-1-4)
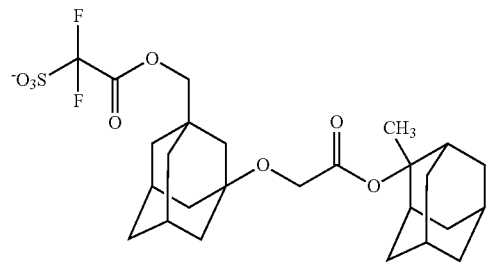

(a1-1-5)
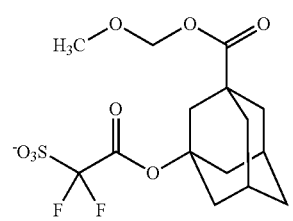

(a1-2-1)
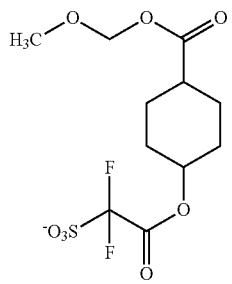

(a1-3-1)
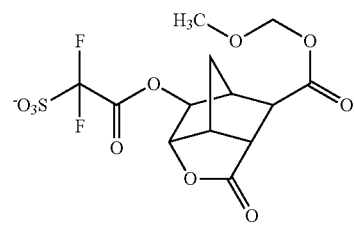

(a1-4-1)
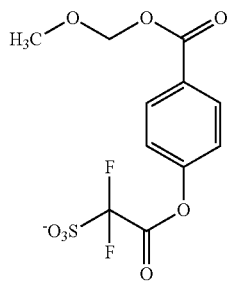

(a1-5-1)
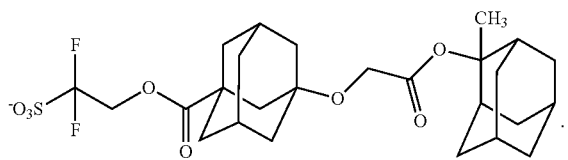

5. The salt according to claim 1, wherein $Z^+$ is a cation represented by formula (a2-1) or (a2-2):

[Chemical Formula 5]

(a2-1)

wherein $R^{a8}$ to $R^{a10}$ each independently represent a linear, branched or cyclic $C_{1-30}$ aliphatic hydrocarbon group or a $C_{6-18}$ aromatic hydrocarbon group, at least one hydrogen atom of the aliphatic hydrocarbon group or the aromatic hydrocarbon group may be replaced with a halogen atom, a hydroxyl group, a linear or branched $C_{1-12}$ alkoxy group, a glycidyloxy group or a $C_{2-4}$ acyl group, at least one hydrogen atom of the aliphatic hydrocarbon group may be replaced with a $C_{6-18}$ aromatic hydrocarbon group, and the aromatic hydrocarbon group may have a linear, branched or cyclic $C_{1-36}$ aliphatic hydrocarbon group as a substituent, (a2-2)
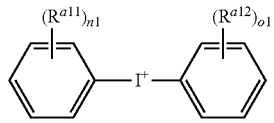

wherein $R^{a11}$ and $R^{a12}$ each independently represent a hydroxyl group, a linear or branched $C_{1-12}$ aliphatic hydrocarbon group, or a linear or branched $C_{1-12}$ alkoxy group, n1 and o1 each independently represent 0 or 1, when n1 or o1 is 0, it means that corresponding substituent is absent.

6. The salt according to claim 5, wherein $Z^+$ is a cation represented by formula (a2-1-1):

[Chemical Formula 6]

(a2-1-1)
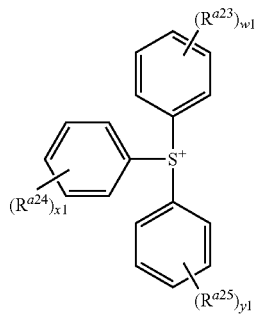

wherein $R^{a23}$ to $R^{a25}$ each independently represent a hydroxyl group, a halogen atom, a linear, branched or cyclic $C_{1-36}$ aliphatic hydrocarbon group, or a linear or branched $C_{1-12}$ alkoxy group, at least one of hydrogen atom of the aliphatic hydrocarbon group may be replaced with a halogen atom, a hydroxyl group, a linear or branched $C_{1-12}$ alkoxy group, a $C_{6-12}$ aromatic hydrocarbon group, a glycidyloxy group or a $C_{2-4}$ acyl group, w1, x1 and y1 each independently represent an integer ranging from 0 to 3, and when w1 represents 0, it means that $R^{a23}$ is absent, when x1 represents 0, it means that $R^{a24}$ is absent, and when y1 represents 0, it means that $R^{a25}$ is absent, and when any of w1 to y1 is 2 or more, a plurality of $R^{a23}$ to $R^{a25}$, respectively, may be the same or different from each other.

7. An acid generator comprising the salt according to any one of claims 1 to 6.

8. A resist composition comprising the salt according to any one of claims 1 to 6 and a resin which becomes soluble in an aqueous alkali solution by the action of an acid.

9. The resist composition according to claim 8, further comprising a basic compound.

* * * * *